US011298381B2

(12) United States Patent
Majeed et al.

(10) Patent No.: US 11,298,381 B2
(45) Date of Patent: Apr. 12, 2022

(54) **MODULATION OF IMMUNE FUNCTION BY *BACILLUS COAGULANS***

(71) Applicants: Muhammed Majeed, Bangalore (IN); Kalyanam Nagabhushanam, East Windsor, NJ (US); Furqan Ali, Bangalore (IN); Sivakumar Arumugam, Bangalore (IN); Shaheen Majeed, Springville, UT (US); Lakshmi Mundkur, Bangalore (IN); Anurag Pande, East Windsor, NJ (US)

(72) Inventors: Muhammed Majeed, Bangalore (IN); Kalyanam Nagabhushanam, East Windsor, NJ (US); Furqan Ali, Bangalore (IN); Sivakumar Arumugam, Bangalore (IN); Shaheen Majeed, Springville, UT (US); Lakshmi Mundkur, Bangalore (IN); Anurag Pande, East Windsor, NJ (US)

(73) Assignee: SAMI LABS LIMITED, Bangalore (IN)

( * ) Notice: Subject to any disclaimer, the term of this patent is extended or adjusted under 35 U.S.C. 154(b) by 202 days.

(21) Appl. No.: 16/396,876

(22) Filed: Apr. 29, 2019

(65) Prior Publication Data
US 2019/0328798 A1 Oct. 31, 2019

Related U.S. Application Data

(60) Provisional application No. 62/664,354, filed on Apr. 30, 2018.

(51) Int. Cl.
*A01N 63/00* (2020.01)
*A61K 35/742* (2015.01)
*C12N 1/20* (2006.01)

(52) U.S. Cl.
CPC .............. *A61K 35/742* (2013.01); *C12N 1/20* (2013.01)

(58) Field of Classification Search
None
See application file for complete search history.

(56) References Cited

U.S. PATENT DOCUMENTS

2018/0338508 A1* 11/2018 Majeed ..................... A23F 5/36

OTHER PUBLICATIONS

Majeed et al. Journal of Toxicology vol. 6, issue 1, pp. 1-9, 2016 (Year: 2016).*
Guidelines for the evaluation of probiotics in food, Joint FAO/WHO Working Group Report on Drafting Guidelines for the Evaluation of Probiotics in Food, London, Ontario, Canada, Apr. 30 and May 1, 2002.
McFarland et al., Strain-Specificity and Disease-Specificity of Probiotic Efficacy: A Systematic Review and Meta-Analysis, Frontiers in Medicine, May 7, 2018;5:124. doi: 10.3389/fmed.2018.00124.
Indian Council of Medical Research/Department of Biotechnology, Ministry of Science and Technology, Government of India, New Delhi, ICMR-DBT Guidelines for Evaluation of Probiotics in Food, 2011.
Marteau, P (2011) Evidence of Probiotic Strain Specificity Makes Extrapolation of Results Impossible From a Strain to Another, Even From the Same Species, Annals of Gastroenterology & Hepatology.
Adams C A The probiotic paradox: live and dead cells are biological response modifiers, Nutr Res Rev. Jun. 2010;23(1):37-46. doi: 10.1017/S0954422410000090.
Liu et al., Macrophage polarization in inflammatory diseases, Int J Biol Sci. May 1, 2014;10(5):520-9.

* cited by examiner

*Primary Examiner* — Jana A Hines
*Assistant Examiner* — Khatol S Shahnan Shah

(57) ABSTRACT

The present invention discloses a composition comprising heat inactivated spores and/or comprising heat inactivated vegetative cells of probiotic bacteria *Bacillus coagulans*, and a process for preparing the same. The invention also discloses a method of modulating immune function in mammals by activating macrophages, using a composition comprising *Bacillus coagulans* in the form of live or heat inactivated spore and/or vegetative cells.

8 Claims, 14 Drawing Sheets

(6 of 14 Drawing Sheet(s) Filed in Color)

Specification includes a Sequence Listing.

A

B

MODULATION OF IMMUNE FUNCTION BY *BACILLUS COAGULANS*

CROSS REFERENCE TO RELATED APPLICATION

This is a non-provisional filing claiming priority from U.S. provisional application No. 62/664,354 filed on 30 Apr. 2018.

BACKGROUND OF INVENTION

Field on Invention

The invention in general relates to probiotics. More specifically, the present invention relates to a novel process for preparing heat inactivated spores/cells of probiotic bacteria *Bacillus coagulans* and its immune modulating function by activating macrophages.

DESCRIPTION OF PRIOR ART

The relation between gut microbiota and immune function is well established. Reports indicate that imbalance in the gut microbiota and inflammation contribute to the development of many health problems including, but not limited to, cardiovascular disease, obesity, cancer, diabetes, arthritis, depression, and inflammatory bowel diseases.

Probiotics have been reported to modulate immune function thereby conferring protection against the development of many diseases. The ability of probiotics to modulate immune function is described in the following prior art documents 1. Jensen et al. GanedenBC30™ cell wall and metabolites: anti-inflammatory and immune modulating effects in vitro, BMC Immunology 2010, 11:15.
2. Dong et al., Comparative effects of six probiotic strains on immune function in vitro, British Journal of Nutrition (2012), 108, 459-470.
3. Chunqing et al, Immunomodulatory Effects of Different Lactic Acid Bacteria on Allergic Response and Its Relationship with In Vitro Properties, PLoS ONE (2016), 11(10): e0164697.
4. Benson et al., Probiotic metabolites from *Bacillus coagulans* GanedenBC30™ support maturation of antigen-presenting cells in vitro, World J Gastroenterol 2012; 18(16): 1875-1883.

Macrophages represent innate immune response and are the first line of defense against any injury or infection. They are widely distributed in different organs and assume the function of antigen presentation to T lymphocytes, thus activating the adaptive response. Depending on the microenvironment macrophages can get differentiated into distinct functional phenotypes, referred to as classically activated M1 and alternatively activated M2. The classic M1 macrophage activation in response to IFN-γ is characterized by high capacity to present antigen, which are considered potent effector cells that kill intracellular pathogens (Benoit M, Desnues B, Mege J L (2008) Macrophage polarization in bacterial infections. J Immunol 181:3733-3739). M2 macrophages are involved in scavenging debris, angiogenesis, tissue remodeling and repair, thus promote wound healing and resolution of inflammation (Mantovani A, Sica A, Sozzani S, Allavena P, Vecchi A, Locati M (2004) The chemokine system in diverse forms of macrophage activation and polarization. Trends Immunol 25:677-686).

Macrophage polarization designates ability to switch phenotype and functional characteristics in response to external signals. The 'classically polarized' M1 macrophages could be induced from M0 macrophages by lipopolysaccharide (LPS) or interferon-c (IFN-c), while M1 macrophages show proinflammatory properties because they produce a range of inflammatory cytokines such as IL-1, IL-6, IL-8, IL-12, IL-23, and tumour necrosis factor (TNF)-a, reactive oxygen species and nitric oxide, whereas M2 macrophages are rather anti-inflammatory as they show increased scavenger receptor (SR-A), arginase, growth factors as well as expression of mRNAs [mannose receptor (Cd206) chitinase-like 3 (Chil3 aka Ym1) and resistin-like α (Retnla aka Fizz1). This plasticity in macrophages is essential in regulating inflammation, immune response and tissue remodeling. M1 dominance has a profound role in diseases like chronic inflammatory diseases, atherosclerosis, myocardial infarction, neuroinflammation/degeneration, cellular autoimmunity, metabolic disorders and autoimmune diseases, while M2 dominance has a role in cancer growth, intracellular pathogen growth and immune suppression. The mechanisms of macrophage polarization and their role in immune response are well disclosed in the following prior art documents:

a) Elhelu M. A The Role of Macrophages in Immunology, J Natl Med Assoc. 1983; 75(3): 314-317.
b) Hirayama et al., The Phagocytic Function of Macrophage-Enforcing Innate Immunity and Tissue Homeostasis, Int J Mol Sci. 2018; 19(1): 92.
c) Gordon S, The role of the macrophage in immune regulation, Research in Immunology. 1998; 149(7):685-688.
d) Martinez et al., Macrophage activation and polarization. Front Biosci. 2008; 13:453-461.
e) Murray et al., Macrophage activation and polarization: nomenclature and experimental guidelines, Immunity. 2014; 41(1): 14-20.

Probiotics can actively interact with the mucosal immune system and modulate the immune response. However, the immune modulating ability of probiotics is strain dependent owing to the presence of diverse protein profiles in their cell walls and differing CpG content of their DNA, which results in differential regulation in the production of anti- and pro-inflammatory cytokines and T helper (Th)1/Th2 balance (Dong et al., Comparative effects of six probiotic strains on immune function in vitro, British Journal of Nutrition (2012), 108, 459-470). Also, it is well known in the scientific art that biological effects of probiotics or products thereof are strain specific and cannot be generalised among genera, species and strains (Probiotics: In Depth/NCCIH, U.S. Department of Health and Human Services, National Institutes of Health). Hence there is still an unmet need to find a superior probiotic strain that enhances and/or modulates immune function of the individual, particularly in children and infants where the development of innate immunity against infection is at the least (Simon et al., Evolution of the immune system in humans from infancy to old age, Proc Biol Sci. 2015; 282(1821): 20143085). Further, due to the difficulty in including live probiotics in finished formulations, and given that cell wall metabolites of probiotics elicit immune response, there is an industrial need of formulation containing heat inactivated cells and/or spores of a superior probiotic strain. The present invention solves the above problem by disclosing a heat inactivated cells and spores of probiotic bacteria *Bacillus coagulans* MTCC 5856 for modulating the immune function.

It is the principle object of the invention to disclose a process for preparing heat inactivated cells and spores of probiotic bacteria *Bacillus coagulans*.

It is another object of the invention to disclose the immune modulating function of heat inactivated cells and spores of probiotic bacteria *Bacillus coagulans* by inducing macrophage polarization.

The present invention solves the above objectives and provides further related advantages.

Deposit of Biological Material

The deposit of biological material *Bacillus coagulans* bearing accession number MTCC 5856, mentioned in the instant application has been made on 19 Sep. 2013 at Microbial Type Culture Collection & Gene Bank (MTCC), CSIR-Institute of Microbial Technology, Sector 39-A, Chandigarh-160036, India.

SUMMARY OF THE INVENTION

In a most preferred embodiment, the invention discloses a composition comprising heat inactivated spores of probiotic bacteria *Bacillus coagulans*, and a process for preparing the same.

In another preferred embodiment, the invention discloses a composition comprising heat inactivated vegetative cells of probiotic bacteria *Bacillus coagulans*, and a process for preparing the same.

In yet another most preferred embodiment the invention discloses a method of modulating immune function in mammals, said method comprising step of administering effective concentration of *Bacillus coagulans* in the form of live or heat inactivated spore and/or bacterium to said mammals to bring about the effect of immune modulation by activating macrophages.

Other features and advantages of the present invention will become apparent from the following more detailed description, taken in conjunction with the accompanying images, which illustrate, by way of example, the principle of the invention.

BRIEF DESCRIPTION OF DRAWINGS

The patent or application file contains at least one drawing executed in color. Copies of this patent or patent application publication with color drawing(s) will be provided by the office upon request and payment of the necessary fee.

FIG. 2 B shows microscopic picture of Gram staining of live spores of *Bacillus coagulans* MTCC 5856.

FIG. 2 C shows microscopic picture of spore staining of live spores of *Bacillus coagulans* MTCC 5856.

DESCRIPTION OF PREFERRED EMBODIMENTS

Figure 1:
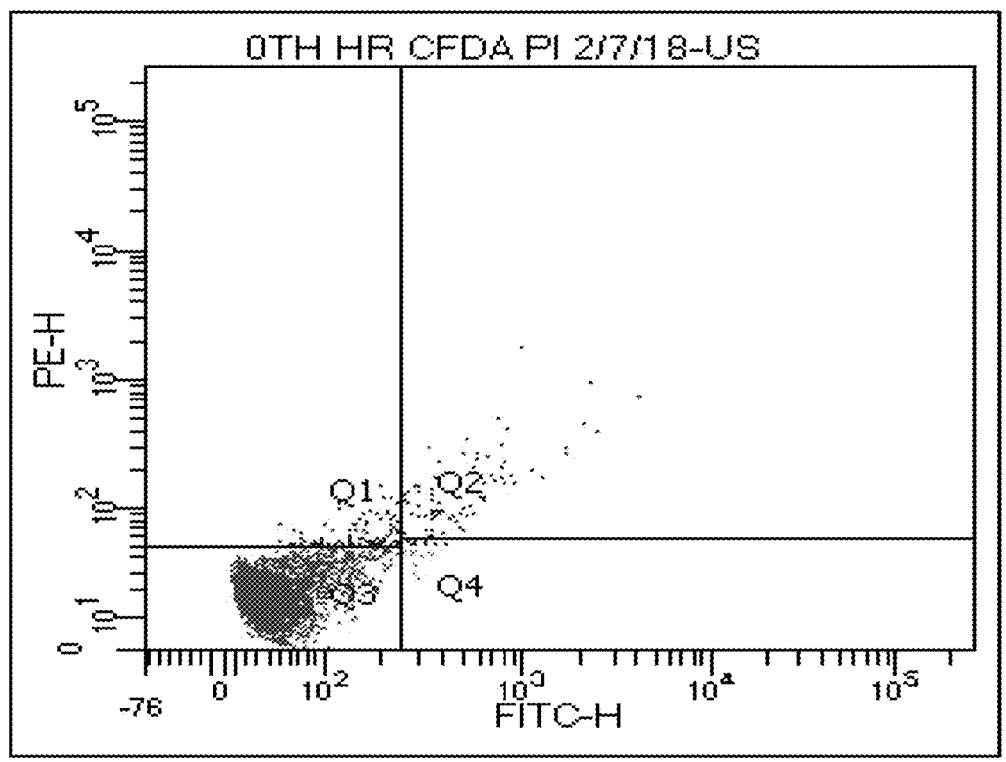
FIG. 1 shows the flow cytomeric results the detection if live and dead cells of heat inactivated spores of *Bacillus coagulans* MTCC 5856 A—Unstained and B—Stained. Q1 denotes dead cells, Q2—Viable but non culturable cells, Q3 denotes damaged cells, and Q4 denotes Live cells.
Figure 1:
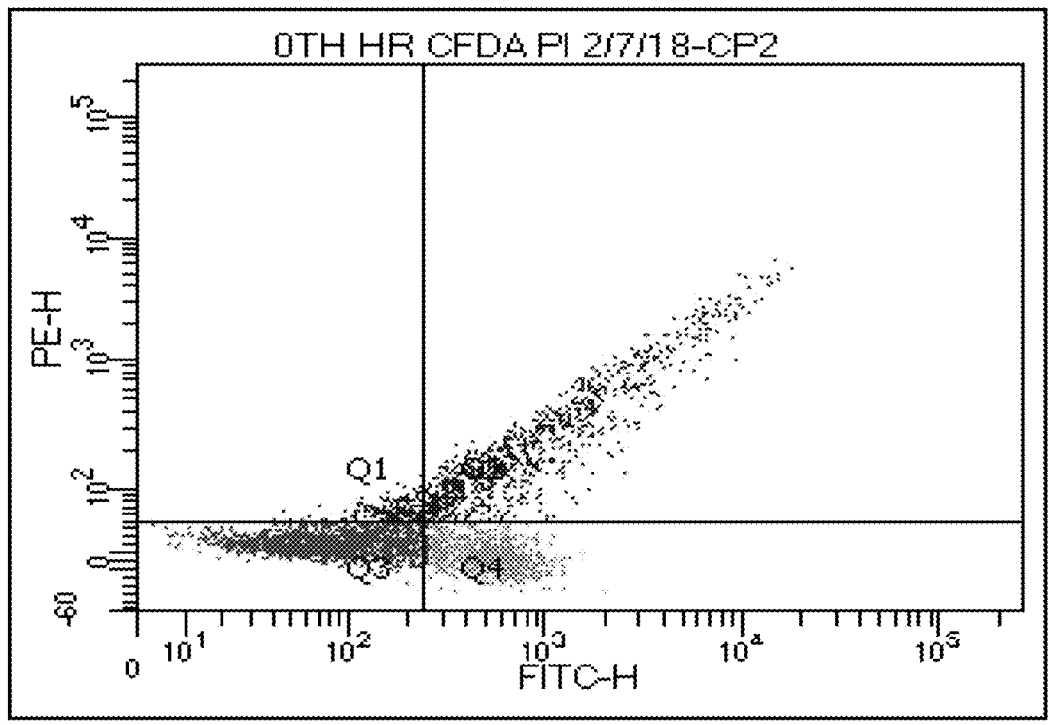

In a most preferred embodiment, the invention discloses a composition comprising heat inactivated spores of probiotic bacteria *Bacillus coagulans*, prepared by the process comprising steps of:
a) Preparing pure culture of *Bacillus coagulans* by inoculating the bacteria in a sterile seed medium and incubating at 37-40° C. for 22-24 hours with constant shaking and confirming the purity through microscopic techniques;
b) Preparing the seed inoculum by mixing the pure culture of step a) in a suitable media and adjusting the pH to 6.5±0.2 with ortho-phosphoric acid;
c) Inoculating the seed medium of step b) to a suitably sterilized fermentation medium (broth) and incubated at 37-39° C. for 35-37 hours with agitation and suitable aeration;
d) Identifying sporulated cells using microscopic techniques and harvesting the spores by centrifuging the broth containing 80-100% sporulated cells, at 7000-15000 rpm;
e) Adding 10% w/v maltodextrin or suitable protective agent to the biomass of sporulated cells in the ratio of 1:1 and filtering the slurry through sterile mesh;
f) Inactivating the slurry of step e) by heat treatment at 110±2° C. with 0.8±0.2 bars of pressure for 5 to 8 hours;
g) Spray drying the heat inactivated spores at 115 to 150° C. inlet temperature and 55 to 70° C. outlet temperature;
h) Subjecting the spray dried powder containing heat inactivated spores to further heat treatment at 121±2° C. with 1.5±0.2 bars of pressure for 15 to 30 minutes to ensure that spore viable count is <$10^3$ cfu/g;
i) Diluting with maltodextrin or suitable protective agent to obtain a composition comprising heat inactivated spores of *Bacillus coagulans*;
j) Enumerating viable, dead and viable but not culturable cells by flow cytometry.

In a related embodiment, the *Bacillus coagulans* strain is specifically *Bacillus coagulans* MTCC 5856. In another related embodiment, the media of step a) and step b) is selected from the group comprising MRS, dextrose media, tryptic soya media, nutrient media, yeast peptone media, corn steep media. In another related embodiment, the fermentation media of step c) is selected from the group comprising MRS, dextrose media, tryptic soya media, nutrient media, yeast peptone media, corn steep media. In another related embodiment, the fermentation media of step c) preferably comprises dextrose, corn steep powder, calcium carbonate, Manganese (II) sulfate and ammonium sulphate.

In another preferred embodiment, the composition is used as a supplement/additive for increasing the immune function in mammals. In a related aspect, the mammal is preferably human. In another related embodiment, the composition comprising heat inactivated spores of *Bacillus coagulans* is formulated with pharmaceutically/nutraceutically accepted excipients, adjuvants and administered in the form of powder, infant formulation, suspension, syrup, emulsion, tablets, capsules, eatable or chewable.

In another most preferred embodiment, the invention discloses a composition comprising heat inactivated vegetative cells of probiotic bacteria *Bacillus coagulans*, prepared by the process comprising steps of:

a) Preparing pure culture of *Bacillus coagulans* by inoculating the bacteria in a sterile seed medium and incubating at 37-40° C. for 22-24 hours with constant shaking and confirming purity through microscopic techniques;
b) Preparing the seed inoculum by mixing the pure culture of step a) in a suitable media and adjusting the pH to 6.5±0.2 with ortho-phosphoric acid;
c) Inoculating the seed medium of step b) to a suitably sterilized fermentation medium (broth) and incubated at 37-39° C. for 35-37 hours with agitation and suitable aeration;
d) Identifying vegetative cells using microscopic techniques and harvesting the cells by centrifuging the broth at 7000-15000 rpm;
e) Adding 10% w/v maltodextrin or suitable protective agent to the biomass of vegetative cells in the ratio of 1:1 and filtering the slurry through sterile mesh;
f) Inactivating the slurry of step e) by heat treatment 100±2° C. with 0.2±0.1 bars of pressure for 5 to 8 hours;
g) Spray drying the heat inactivated vegetative cells at 115 to 150° C. inlet temperature and 55 to 70° C. outlet temperature;
h) Diluting with maltodextrin or suitable protective agent to obtain a composition comprising heat inactivated vegetative cells of *Bacillus coagulans*;
i) Enumerating viable, dead and viable but not culturable cells by flow cytometry.

In a related embodiment, the *Bacillus coagulans* strain is specifically *Bacillus coagulans* MTCC 5856. In another related embodiment, the media of step a) and step b) is selected from the group comprising MRS, dextrose media, tryptic soya media, nutrient media, yeast peptone media, corn steep media. In another related embodiment, the fermentation media of step c) is selected from the group comprising MRS, dextrose media, tryptic soya media, nutrient media, yeast peptone media, corn steep media. In another related embodiment, the fermentation media of step c) preferably comprises dextrose, corn steep powder, calcium carbonate, Manganese (II) sulfate and ammonium sulphate.

In another preferred embodiment, the composition is used as a supplement/additive for increasing the immune function in mammals. In a related aspect, the mammal is preferably human. In another related embodiment, the composition comprising heat inactivated vegetative cells of *Bacillus coagulans* is formulated with pharmaceutically/nutraceutically accepted excipients, adjuvants and administered in the form of powder, infant formulation, suspension, syrup, emulsion, tablets, capsules, eatable or chewable.

In yet another most preferred embodiment the invention discloses a method of modulating immune function in mammals, said method comprising step of administering effective concentration of *Bacillus coagulans* in the form of spore and/or bacterium to said mammals to bring about the effect of immune modulation by polarizing macrophages. In a related embodiment, the spores include viable or heat inactivated or dead spores of *Bacillus coagulans*. In another related embodiment, the bacterium includes viable or heat inactivated or dead or lysed vegetative cells of *Bacillus coagulans*. In another related embodiment, the *Bacillus coagulans* strain is preferably *Bacillus coagulans* MTCC 5856. In a related aspect, the modulation of immune function is brought about by polarizing the macrophages to M1 type. In another related aspect, the polarisation of macrophages to M1 type is brought about by inducing the expression of pro-inflammatory genes and cells surface receptors. In yet another related aspect, the pro-inflammatory genes are selected from the group comprising IL-1β, IL-6, IL-12p40, IL23, TNF-α, and iNOS. In a further related aspect, the cell surface receptors are selected from the group comprising CD80, CD83, CD86, MHC-II, F4/80 and CD16/32. In yet another related embodiment, the mammal is human. In another related embodiment, the composition comprising heat inactivated spores and/or vegetative cells of *Bacillus coagulans* is formulated with pharmaceutically/nutraceutically accepted excipients, adjuvants and administered in the form of powder, infant formulation, suspension, syrup, emulsion, tablets, capsules, eatable or chewable.

The following illustrative examples further describe in detail the preferred embodiments of the invention:

EXAMPLES

Example 1: Process of Heat Inactivation of Spores and Vegetative Cells of *Bacillus coagulans*

Heat inactivation of spores of *Bacillus coagulans* is carried out by the following steps:
a) Preparing pure culture of *Bacillus coagulans* by inoculating the bacteria in a sterile seed medium (MRS, dextrose media, tryptic soya media, nutrient media, yeast peptone media, corn steep media) and incubating at 37-40° C. for 22-24 hours with constant shaking and confirming the purity through microscopic techniques;
b) Preparing the seed inoculum by mixing the pure culture of step a) in a suitable media (MRS, dextrose media, tryptic soya media, nutrient media, yeast peptone media, corn steep media) and adjusting the pH to 6.5±0.2 with ortho-phosphoric acid
c) Inoculating the seed medium of step b) to a suitably sterilized fermentation medium (broth—comprising dextrose, corn steep powder, calcium carbonate, Manganese (II) sulfate and ammonium sulphate) and incubated at 37-39° C. for 35-37 hours with agitation and suitable aeration;
d) Identifying sporulated cells using microscopic techniques and harvesting the spores by centrifuging the broth containing 80-100% sporulated cells, at 7000-15000 rpm;
e) Adding 10% w/v maltodextrin or suitable protective agent to the biomass of sporulated cells in the ratio of 1:1 and filtering the slurry through sterile mesh;
f) Inactivating the slurry of step e) by heat treatment at 110±2° C. with 0.8±0.2 bars of pressure for 5 to 8 hours;
g) Spray drying the heat inactivated spores at 115 to 150° C. inlet temperature and 55 to 70° C. outlet temperature;
h) Subjecting the Spray dried powder containing heat inactivated spores to further heat treatment at 121±2° C. with 1.5±0.2 bars of pressure for 15 to 30 minutes to ensure that spore viable count is $10^3$ cfu/g;
i) Diluting with maltodextrin or suitable protective agent to obtain a composition comprising heat inactivated spores of *Bacillus coagulans*;
j) Enumerating viable, dead and viable but not culturable cells by flow cytometry.

Similarly, the heat inactivated vegetative cells are prepared by the following process:
a) Preparing pure culture of *Bacillus coagulans* by inoculating the bacteria in a sterile seed medium (MRS, dextrose media, tryptic soya media, nutrient media, yeast peptone media, corn steep media) and incubating at 37-40° C. for 22-24 hours with constant shaking and confirming the purity through microscopic techniques;
b) Preparing the seed inoculum by mixing the pure culture of step a) in a suitable media (MRS, dextrose media, tryptic soya media, nutrient media, yeast peptone media, corn steep media) and adjusting the pH to 6.5±0.2 with ortho-phosphoric acid
c) Inoculating the seed medium of step b) to a suitably sterilized fermentation medium (broth—comprising dextrose, corn steep powder, calcium carbonate, Manganese (II) sulfate and ammonium sulphate) and incubated at 37-39° C. for 35-37 hours with agitation and suitable aeration;
d) Identifying vegetative cells using microscopic techniques and harvesting the cells by centrifuging the broth at 7000-15000 rpm;
e) Adding 10% w/v maltodextrin or suitable protective agent to the biomass of vegetative cells in the ratio of 1:1 and filtering the slurry through sterile mesh;
f) Inactivating the slurry of step e) by heat treatment 100±2° C. with 0.2±0.1 bars of pressure for 5 to 8 hours;
g) Spray drying the heat inactivated vegetative cells at 115 to 150° C. inlet temperature and 55 to 70° C. outlet temperature;
h) Diluting with maltodextrin or suitable protective agent to obtain a composition comprising heat inactivated vegetative cells of *Bacillus coagulans*;
i) Enumerating viable, dead and viable but not culturable cells by flow cytometry.

Figure 2A:
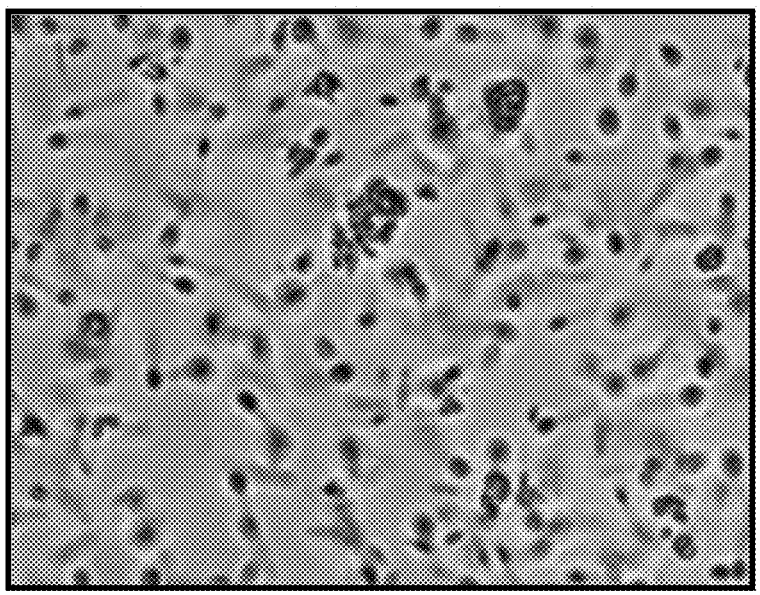
FIG. 2 A shows microscopic picture of wet mount of live spores of *Bacillus coagulans* MTCC 5856.
FIG. 2D shows microscopic picture of wet mount of heat inactivated spores of *Bacillus coagulans* MTCC 5856.
FIG. 2E shows the microscopic picture of Gram stain of heat inactivated spores of *Bacillus coagulans* MTCC 5856.
FIG. 2F shows the spores staining of heat inactivated spores of *Bacillus coagulans* MTCC 5856.
Figure 2B:
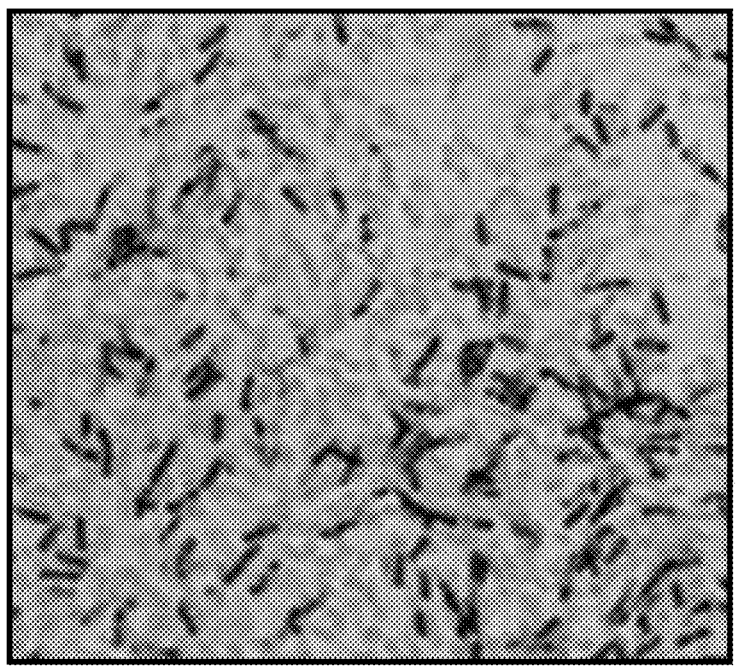
Figure 2C:
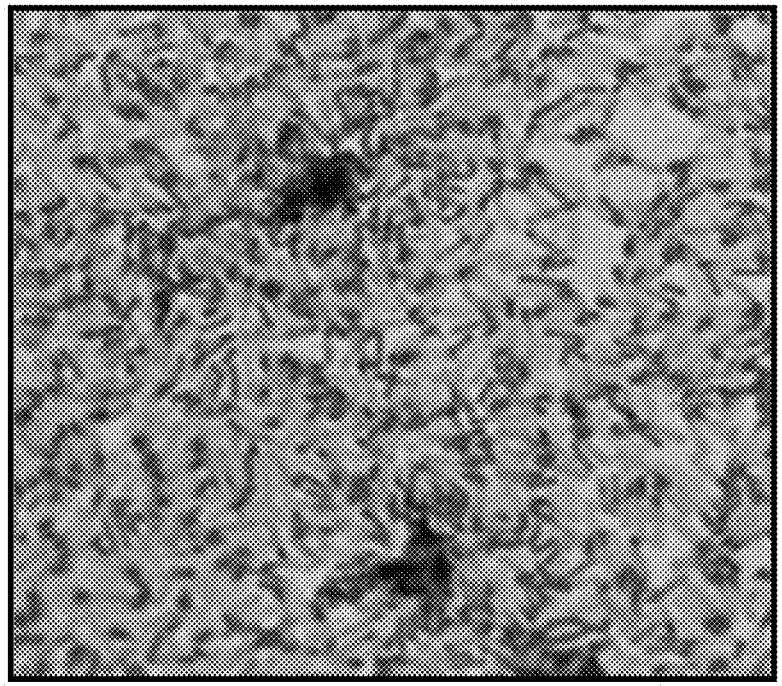
Figure 2D:
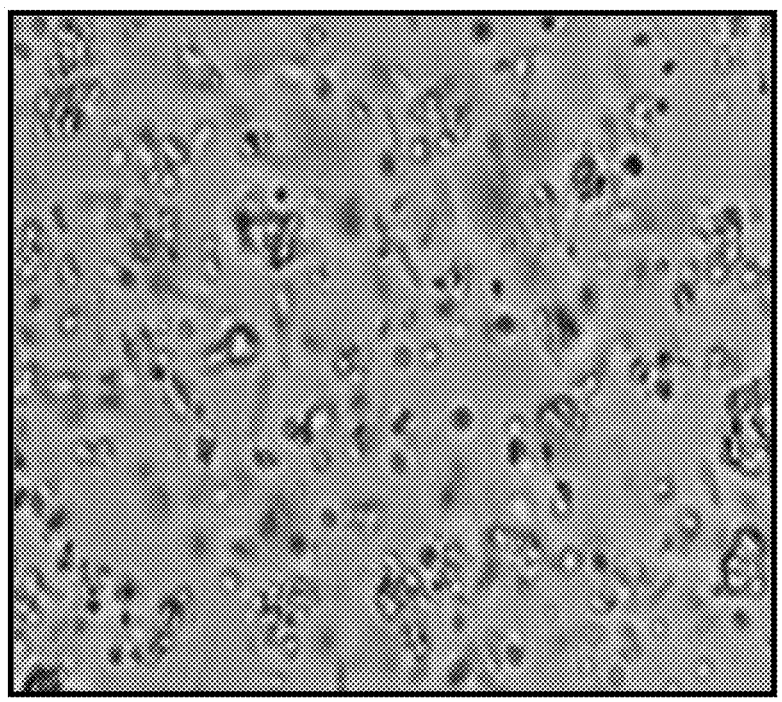
Figure 2E:
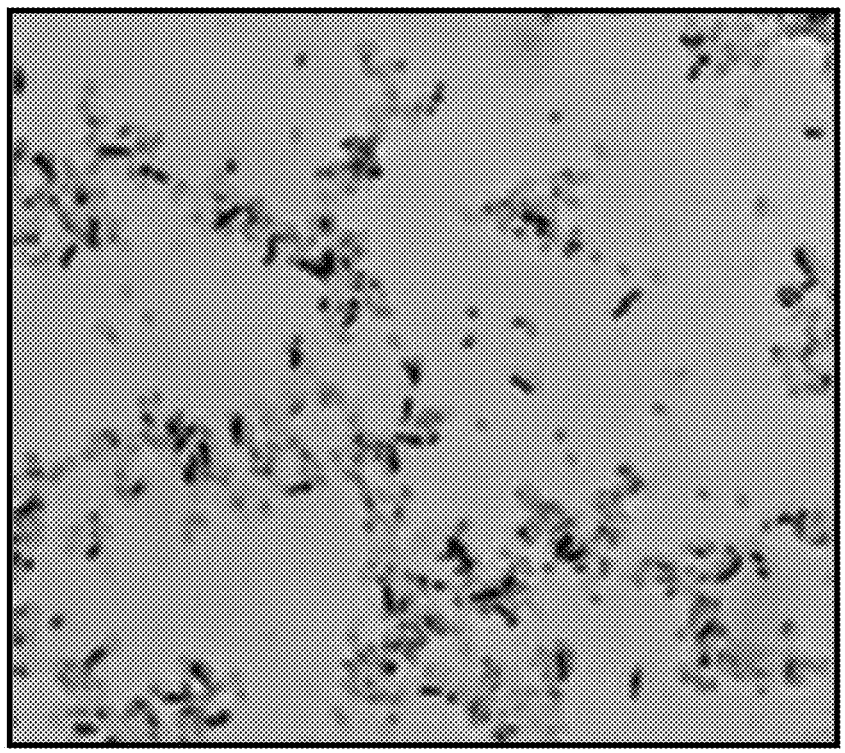
Figure 2F:
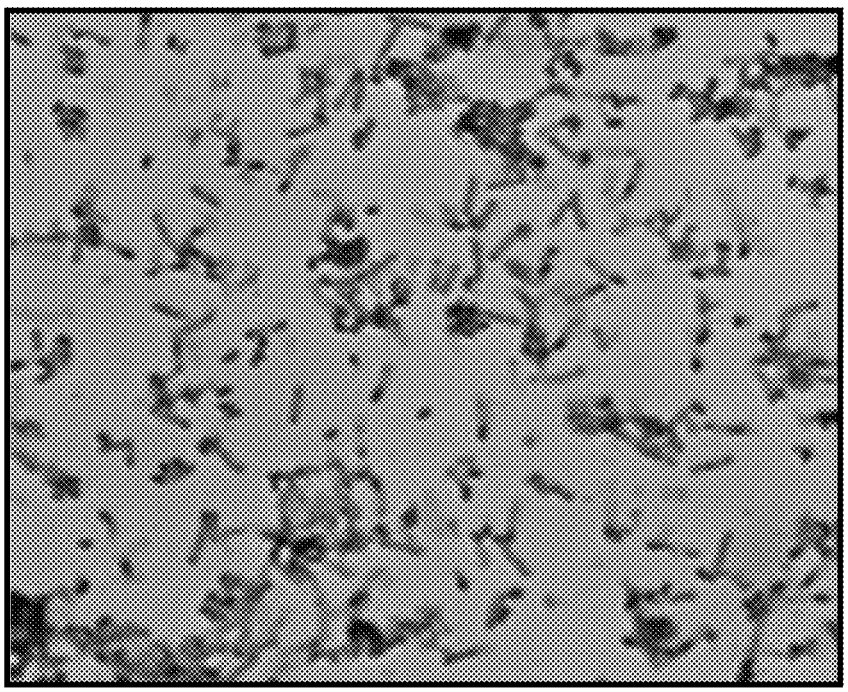
Figure 3A:
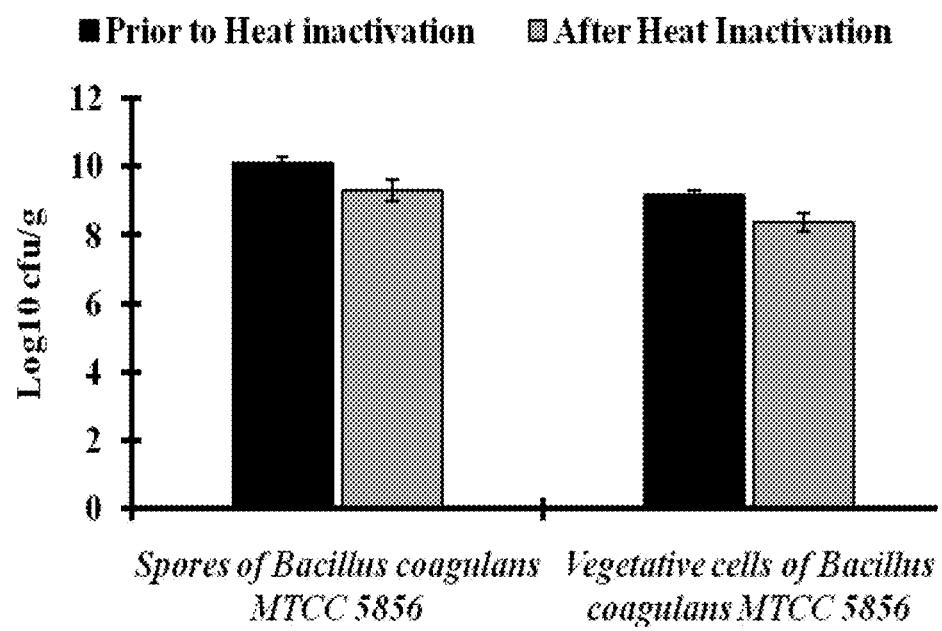
FIG. 3A is the graphical representation showing the effect of heat inactivation on the viability of spores and vegetative cells of *Bacillus coagulans* MTCC 5856 determined by following Flow Cytometry (FCM) technique.
Figure 3B:
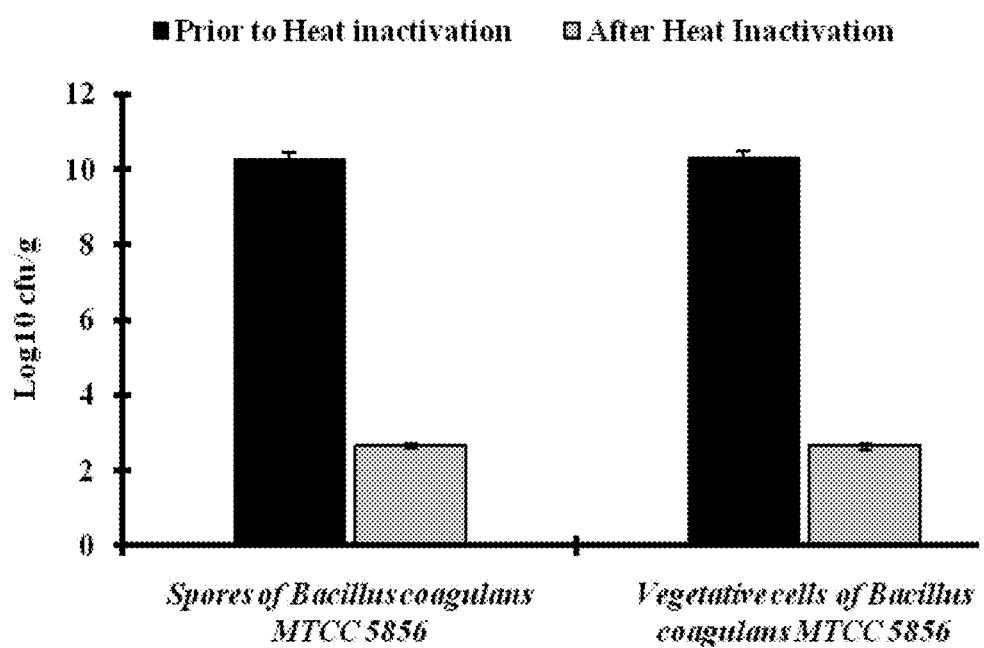
FIG. 3B is the graphical representation showing the effect of heat inactivation on the viability of spores and vegetative cells of *Bacillus coagulans* MTCC 5856 determined by following plate count method.

The flow cytometric results differentiate viable but non-culturable cells, from dead and live cells (FIG. 1A and FIG. 1B). The heat inactivation step is vital for preparing a stable composition responsible for the biological function of a probiotic strain. If the heat provided is inadequate, it leads to partial inactivation and if the heat is more, the spores die and cannot be revived. Hence, the right temperature as mentioned in the above steps was decided through rigorous experimentation which shows that the cell integrity is maintained (FIG. 2A-2F) after heat inactivation which resulted in retaining the biological function of such composition containing heat inactivated spores and/or vegetative cells of probiotic strain. FIGS. 2A, 2B and 2C shows the morphology live spores of *Bacillus coagulans* whereas FIGS. 2 D, 2E and 2F show the morphology of heat inactivated spores of *Bacillus coagulans*. It is evident that the heat inactivation step has not significantly changed the cell morphology/structure, thus, found to be suitable for preparing a stable composition which exhibits biological function i.e. modulating immune function. The viability of the cells was determined by flow cytometric method (FIG. 3A) and plate count (FIG. 3B). For determining viable cells, the flow cytometric method is much more efficient than plate count method. It is very clear from the flow cytometric data (FIG. 1A, FIG. 1B and FIG. 3A) that the heat inactivated spores and vegetative cells obtained by following said process had viable vegetative cells and spores of *Bacillus coagulans* but they were not culturable as indicated by the plate method of vegetative cells and spores of *Bacillus coagulans* enumeration (FIG. 3B)

Example 2: Modulation of Immune Function by Macrophage Polarisation

Experimental Section/Materials and Methods

Reagents

Dulbecco's modified eagle's medium (DMEM), LPS (*Escherichia coli* 055:B5), and FITC-dextran (40,000 Da) were purchased from Sigma Chemical Co. (St. Louis, Mo.). Kits for Cell Counting (Kit-8), nitric oxide (NO), BCA protein, and nitric oxide synthase (iNOS) were purchased from Beyotime Biotechnology (Haimen, China). Antimouse antibodies FITC-CD80, FITC-CD83, APC-CD86, APC-MHCII, FITC-F4/80 pro-inflammatory markers were purchased from Beijing 4A Biotech Co., Ltd (4A Biotech, china. Eosin-methylene blue medium (EMB) agar were obtained from solarbio (solarbio, china). Phospho-ERK1/2, ERK1/2, phospho-JNK, INK, phospho-p38, p-38, β-actin and HRP-conjugated anti-mouse IgG were obtained from Cell Signaling Technology (Massachusetts, USA).

Cell Culture and Probiotics

The mouse monocyte/macrophage cell line, Raw264.7, was grown in Dulbecco's modified Eagle's medium (DMEM) supplemented with 10% heat-inactivated fetal bovine serum (Gibco, USA), 100 μg/mL streptomycin, and 100 U/mL, penicillin (Sigma-Aldrich, USA). Cells were maintained at 37° C. in a humidified atmosphere of 5% CO2. *B. coagulans* MTCC 5856 commercially known as LactoSpore®, Registered trademark of Sabinsa Corporation, USA) and heat inactivated vegetative cells and heat inactivated spores were used for the experimentation.

Cell Viability Assay

Cells were seeded at $2 \times 10^4$ cells/well in 96-well culture plates and incubated for 6 h. then RAW264.7 cells were further cultured with PBS, Lipopolysaccharide (LPS, 200 ng/mL) for 24 h or live cells ($1.5 \times 10^8$ cfu/mL) and heat inactivated spores ($1.5 \times 10^8$ cfu/mL) respectively for 6 h. Stimulation with LPS (200 ng/ml) was included in each experiment to ensure functional differentiation into M1 subtypes. Cell counting kit-8 (Beyotime) was used to determine the cell cytotoxicity according to the manufacturer's instruction. Briefly, 10 μl CCK-8 was added into each well and incubated for 1-4 h at 37° C. The optical absorbance at OD450 was measured by SpectraMax M5 (Molecular Devices, Sunnyvale, Calif.).

Relative Transcription of iNOS, IL-1β, IL-6, IL-12p40 and TNF-α

After treatment of RAW264.7 cells ($1.0 \times 10^6$ cells in six-well plates) with either Lipopolysaccharide (LPS, 200 ng/mL) for 24 h or live cells ($1.5 \times 10^8$ cfu/mL), heat inactivated cells or heat inactivated spores ($1.5 \times 10^8$ cfu/mL alone for 6 h at 37° C. under 5% CO2, Macrophages were lysed and total RNA was extracted using Trizol (Sangon Biotech). The concentration, purity, and quality of isolated RNA were measured with a NanoDrop One spectrophotometer (ThermoFisher Scientific) and 1,000 ng of total RNA was immediately reverse transcribed into cDNA using HiScript® II Q RT SuperMix (Vazyme, R223-01). Relative expression levels of iNOS, IL-1β, IL-6, IL-12p40 and TNF-α were evaluated by quantitative real-time reverse transcription PCR (RT-qPCR), using ChamQTM SYBR® qPCR Master Mix (Vazyme, Q341-02) and CFX96 Real Time PCR System (Bio-Rad). The RT-qPCR comprised an initial step of 95° C. for 10 min, thereafter 95° C. for 15 s followed by 40 cycles of 95° C. for 15 s and 60° C. for 1 min. All data were normalized to the level of actin transcripts amplified from the same sample, and then to untreated control mRNA. The data were analyzed with 2-ΔΔT method. The gene-specific primer sequences are given below:

IL-1β
F: GCAACTGTTCCTGAACTCAACT (SEQ ID NO: 1)

R: ATCTTTTGGGGTCCGTCAACT (SEQ ID NO: 2)

IL-6
F: TAGTCCTTCCTACCCCAATTTCC (SEQ ID NO: 3)

R: TTGGTCCTTAGCCACTCCTTC (SEQ ID NO: 4)

IL-12p40
F: CCCATTCCTACTTCTCCCTCAA (SEQ ID NO: 5)

R: CCTCCTCTGTCTCCTTCATCTT (SEQ ID NO: 6)

TNF-α
F: CCCTCACACTCAGATCATCTTCT (SEQ ID NO: 7)

R: GCTACGACGTGGGCTACAG (SEQ ID NO: 8)

iNOS
F: CTCACCTACTTCCTGGACATTAC (SEQ ID NO: 9)

R: CAATCTCTGCCTATCCGTCTC (SEQ ID NO: 10)

β-actin
F: CGTTGACATCCGTAAAGACC (SEQ ID NO: 11)

R: AACAGTCCGCCTAGAAGCAC (SEQ ID NO: 12)

Evaluation of Nitric Oxide Synthesis

Monolayers of RAW 264.7 macrophages in 12-well microplate were cultured in DMEM supplemented with 10% FBS at 37° C. in 5% CO2 under optimal humidity. Cells were incubated with PBS, Lipopolysaccharide (LPS, 200 ng/mL) for 24 h, live cells ($1.5 \times 10^8$ cfu/mL) and heat inactived spores ($1.5 \times 10^8$ cfu/mL) respectively. Nitric Oxide and Nitric Oxide Synthase (iNOS, tNOS) in supernatant was determined using Nitric Oxide and Nitric Oxide Synthase typed assay kit (Nj jiancheng, China).

Cytokine Profile

The concentrations of iNOS, NO, IL-1β, IL-6 TNF-α and TGF-β secreted by macrophages after treatment of LPS or $1.5 \times 10^8$ cfu/ml *Bacillus coagulans* (live cells, heat inactivated spores) were determined in macrophage cells supernatants by ELISA (4A Biotech, china) following the manufacturer's recommendation. The cytokines levels were determined by comparison with a standard calibration curve.

Dextran Phagocytosis Assay

RAW264.7 cells were seeded at $1.0 \times 10^5$ cells in 12-well plates followed by treatment with either Lipopolysaccharide (LPS, 200 ng/mL) for 24 h or live cells ($1.5 \times 10^8$ cfu/mL) or heat inactivated spores ($1.5 \times 10^8$ cfu/mL) for 6 h at 37° C. under 5% $CO_2$, following 1 h starvation in serum-free medium. Then, cells were washed with PBS for two times repeat and incubated with FITC-dextran (1 mg/mL; Sigma, FD40S) for 1 h at 37° C. under 5% $CO_2$. Thereafter, cells were washed with PBS and harvested followed by centrifugation (500×g, 5 min, 4° C.). Data were processed using flow cytometry analysis (FACS) at least 10,000 events to determine Mean fluorescence intensity (MFI) of intracellular FITC-dextran.

Flow Cytometric Analysis

RAW264.7 cells were seeded at $1.0 \times 10^5$ cells in 12-well plates followed by treatment with either Lipopolysaccharide (LPS, 200 ng/mL) for 24 h or live cells ($1.5 \times 10^8$ cfu/mL) alone or heat inactivated spores ($1.5 \times 10^8$ cfu/mL) for 6 h at 37° C. under 5% CO2. After the final incubation, macrophages were washed with PBS and treated with 0.04% ethylenediamine tetra acetic acid (EDTA, Sinopharm), Cells were incubated with Fc Block TM (BD Biosciences), and stained with either an FITC anti-mouse CD80, FITC anti-mouse CD83, APC anti-mouse CD86, APC anti-mouse MHCII, FITC anti-mouse F4/80 and FITC anti-mouse CD16/32 antibody (BioLegend) or an isotype control, 30 min, 4° C. in the dark. After washing with PBS for two times repeat, stained cells were analyzed by fluorescence-activated cell sorting (FACS) for at least 10,000 events to determine Mean fluorescence intensity (MFI).

Statistical Analysis

Data are presented as means±SEM at least three independent experiments. Statistical analysis was performed using SPSS20.0 and OriginPro Software. Statistical significance was assessed using a one-way analysis of variance followed by Dunnett's or Tukey's test for multiple comparisons. The value of $P<0.05$ was considered as statistical significant.

Results

Viability Analysis of Bacillus coagulans on RAW264.7 Macrophage

Figure 4:
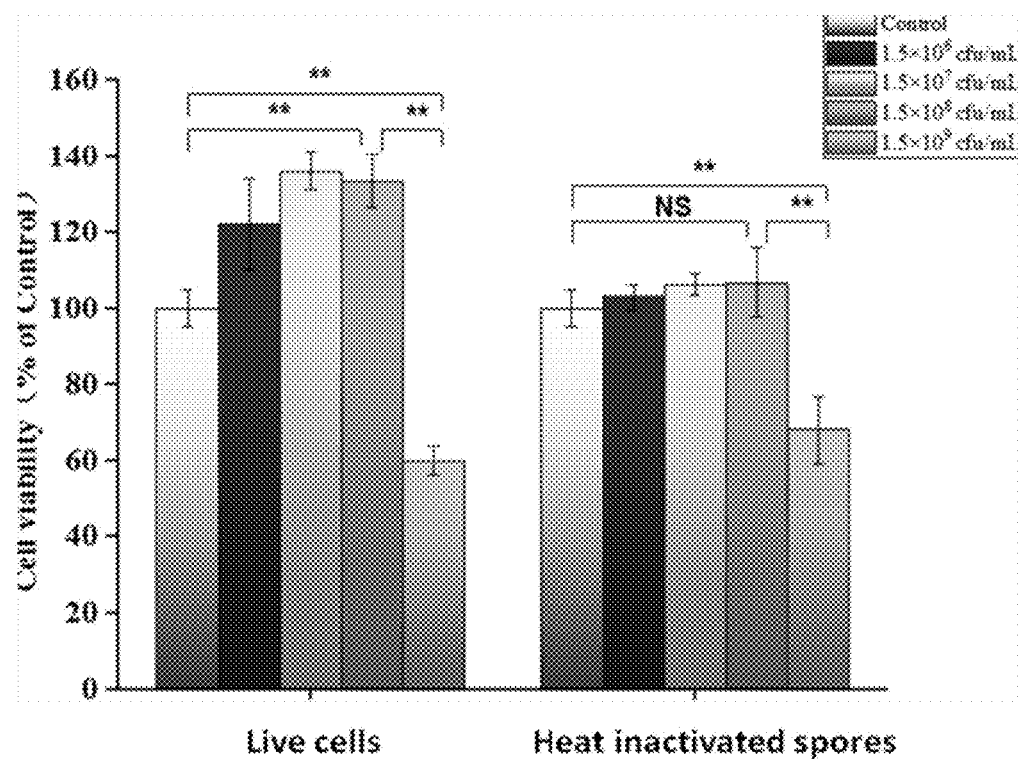
FIG. 4 is the graphical representation showing Cell viability of RAW264.7 cells following treatment with different probiotic concentration. Treatment was done at concentration of $1.5 \times 10^6$, $1.5 \times 10^7$, $1.5 \times 10^8$, $1.5 \times 10^9$ cfu/ml at 6 h points.

To evaluate the cytotoxicity of probiotic strain Bacillus coagulans (Live cells and heat inactivated cells) on murine macrophage cell line, RAW264.7 cells were treated with probiotic Bacillus coagulans for 6 h and cell viability was determined using the CCK-8 assay. In this assay, no significant decrease ($p>0.05$) of viability was observed when RAW264.7 cells were treated with Live cells or Heated inactivated spores at a range of concentrations (from $1.5\times 10^6$ to $1.5\times 10^8$ cfu/ml) (FIG. 4). However, viability was decreased when cells were exposure to $1.5\times 10^9$ cfu/ml Bacillus coagulans ($P<0.05$). At $1.5\times 10^8$ cfu/ml Live cells were found to increase cell viability ($P<0.01$) compared with the control. Therefore, $1.5\times 10^8$ cfu/ml were used in subsequent experiments.

Figure 5A:
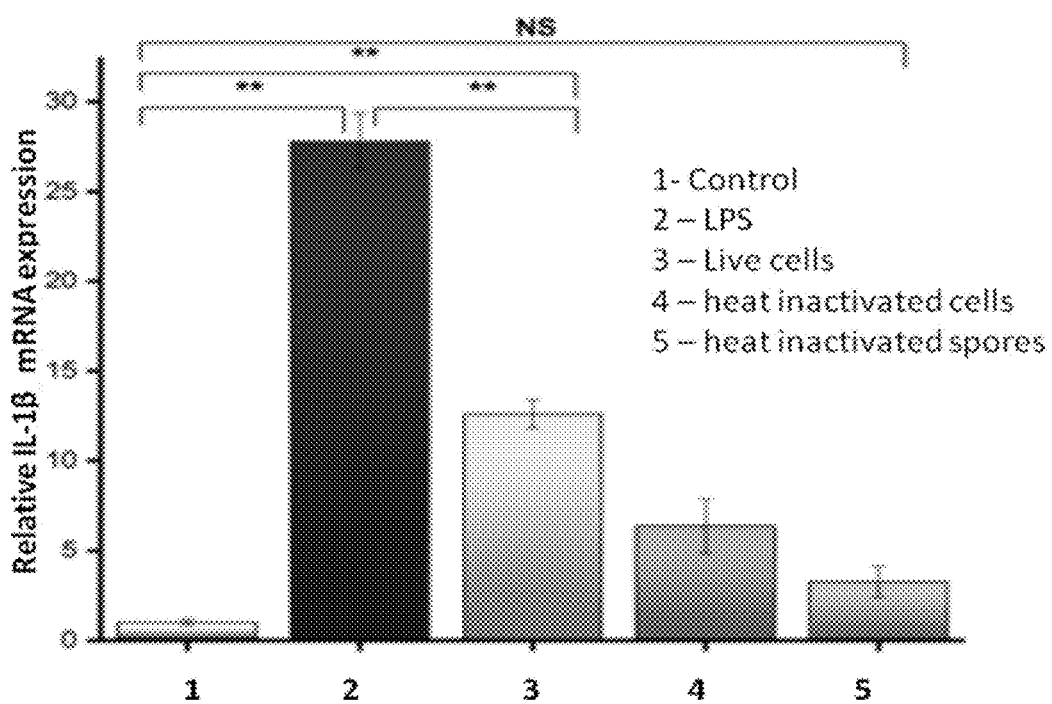
FIG. 5A is the graphical representation showing the expression of IL-1β gene in RAW 264.7 co-culture with $1.5 \times 10^8$ cfu/ml live cells, heat inactivated cells and heat inactivated spores for a duration of 6 h
Figure 5B:
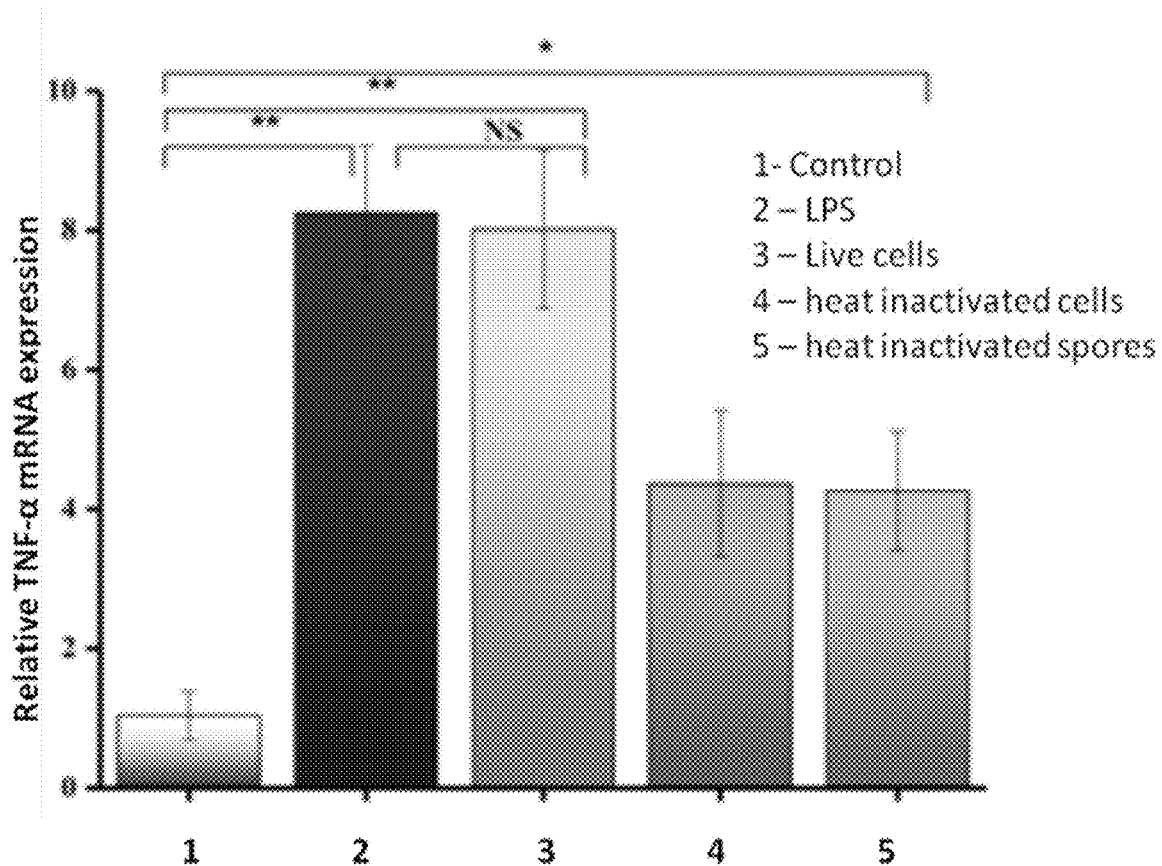
FIG. 5B is the graphical representation showing the expression of TNF-α gene in RAW 264.7 co-culture with $1.5 \times 10^8$ cfu/ml live cells, heat inactivated cells and heat inactivated spores for a duration of 6 h.
Figure 5C:
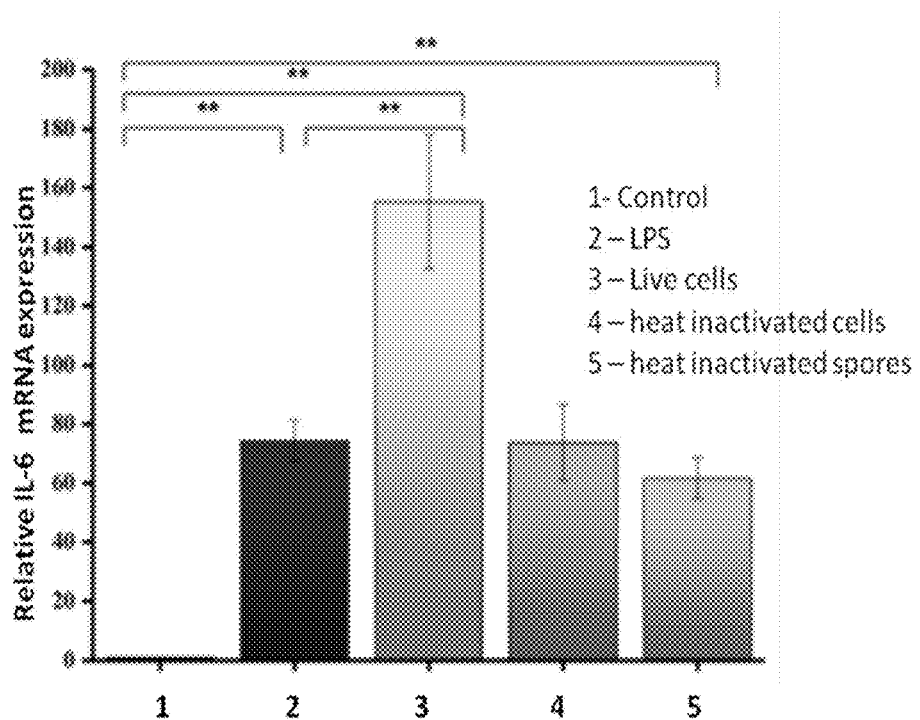
FIG. 5C is the graphical representation showing the expression of IL-6 gene in RAW 264.7 co-culture with $1.5 \times 10^8$ cfu/ml live cells, heat inactivated cells and heat inactivated spores for a duration of 6 h.
Figure 5D:
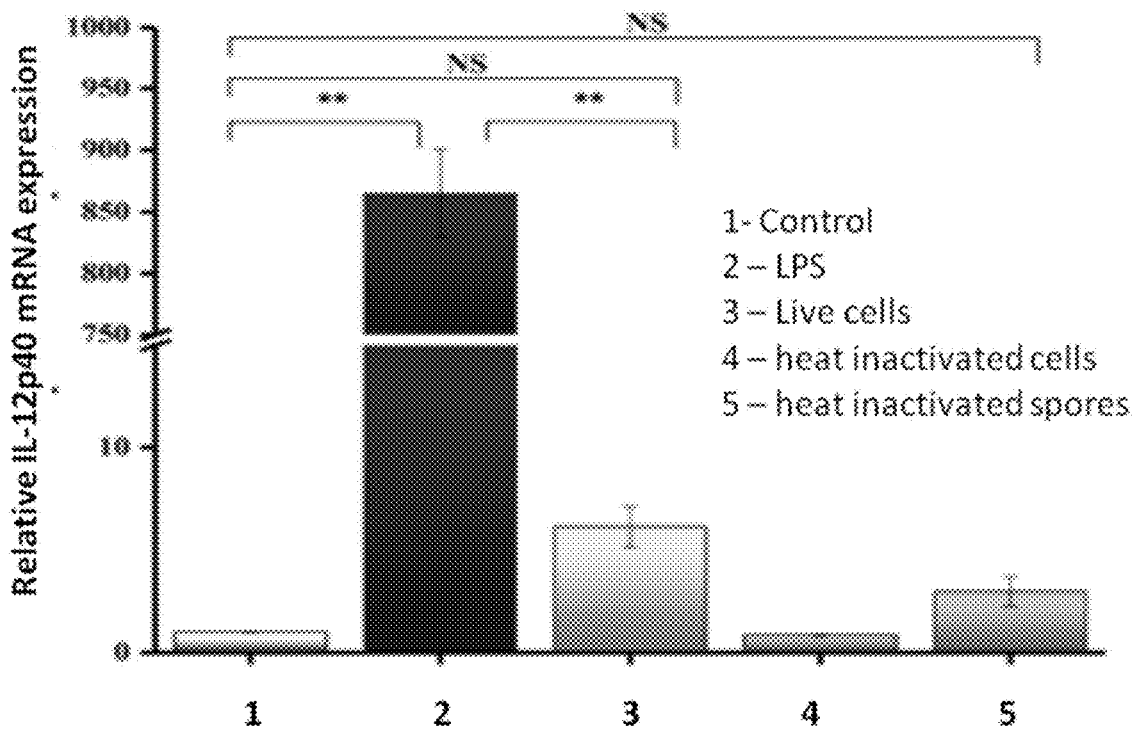
FIG. 5D is the graphical representation showing the expression of IL-12p40 gene in RAW 264.7 co-culture with $1.5 \times 10^8$ cfu/ml live cells, heat inactivated cells and heat inactivated spores for a duration of 6 h.
Figure 6:
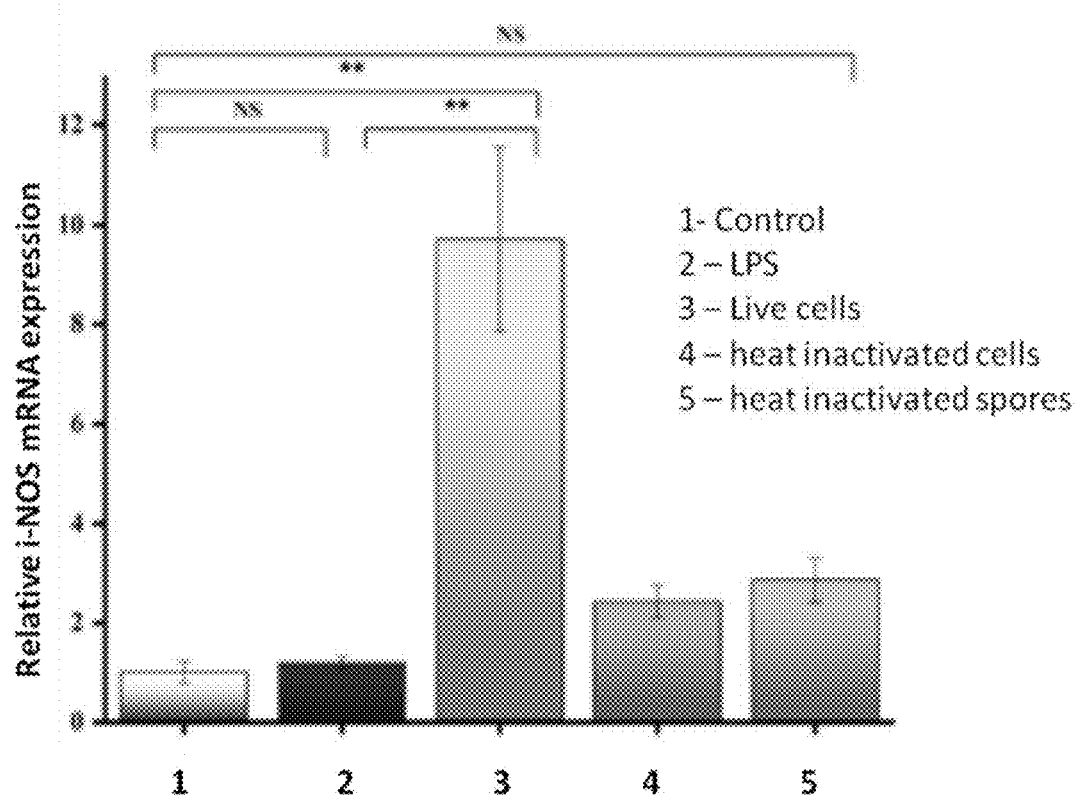
FIG. 6 is the graphical representation showing the expression of i-NOS gene in RAW 264.7 co-culture with $1.5 \times 10^8$ cfu/ml live cells, heat inactivated cells and heat inactivated spores for a duration of 6 h.

Bacillus coagulans Upregulates the Gene Expression Level of Markers for M1 Macrophage In Vitro The expression of pro-inflammatory genes (IL-1 β, IL-6, IL-12p40, TNF-α) and iNOS was evaluated following treatment of RAW 264.7 with $1.5\times 10^8$ cfu/ml Bacillus coagulans (Live cells, heat inactivated cells and heat inactivated spores) for a duration of 6 h. mRNA level revealed proinflammatory genes except for IL-12p40 were dramatically increased ($P<0.01$) in RAW 264.7 treated with live cells and LPS treatment relative to untreated time-matched control cells (FIG. 5A-5D). Furthermore, heat inactivated spores up-regulate expression of IL-6 ($P<0.01$) and TNF-α ($P<0.05$) (FIG. 5C,5B). The probiotic Live cells significantly upregulated ($P<0.01$) the expression of iNOS, compared to untreated samples, showing a higher potency compared to LPS. (FIG. 6). Nevertheless, it is noteworthy that Bacillus coagulans tended to induce up-regulation of iNOS which indicated live cells has a complex role in promoting macrophage Raw264.7 polarization.

Figure 7:
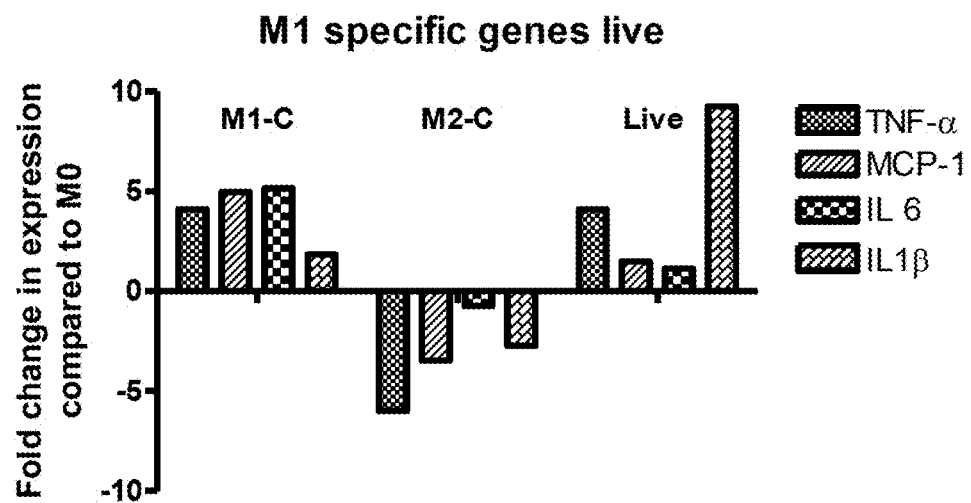
FIG. 7 is the graphical representation showing the expression of M1 related genes activated by live cells of *Bacillus coagulans* MTCC 5856.

Alternatively, human monocytes THP1 cells were treated with PMA to differentiate them to macrophages. These macrophages were cultured in low serum containing media to induce a M0 phase. M1 macrophages were differentiated using bacterial LPS and IFN-γ to induce an M1 polarization (Micontrol) and IL4 to induce M2 polarization (M2 control). M0 cells were incubated with live cells (1000 cells) for 6 hours. Cells were washed and processed for RNA isolation and RT PCR. Supernatants stored for cytokine estimation The results indicated that Bacillus coagulans MTCC 5856 (live cells) was found to induce a M1 phenotype by increasing the expression of genes related to M1 phenotype (TNF-α, MCP-1, IL6, IL 1β) (FIG. 7).

Bacillus coagulans Induced the Immune Response of RAW264.7 Macrophages

Figure 8A:
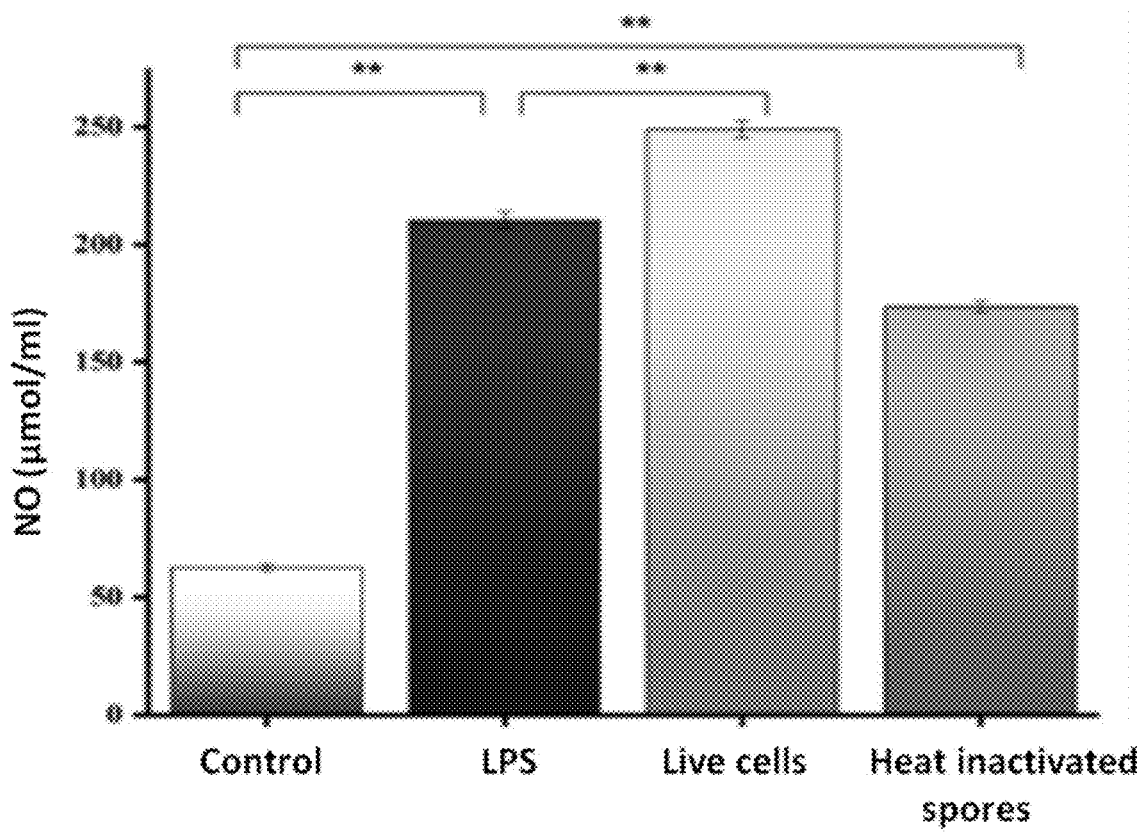
FIG. 8A is the graphical representation showing the levels of NO in RAW 264.7 cells cultured with live cells, heat inactivated cells and heat inactivated spores of *Bacillus coagulans* MTCC 5856.
Figure 8B:
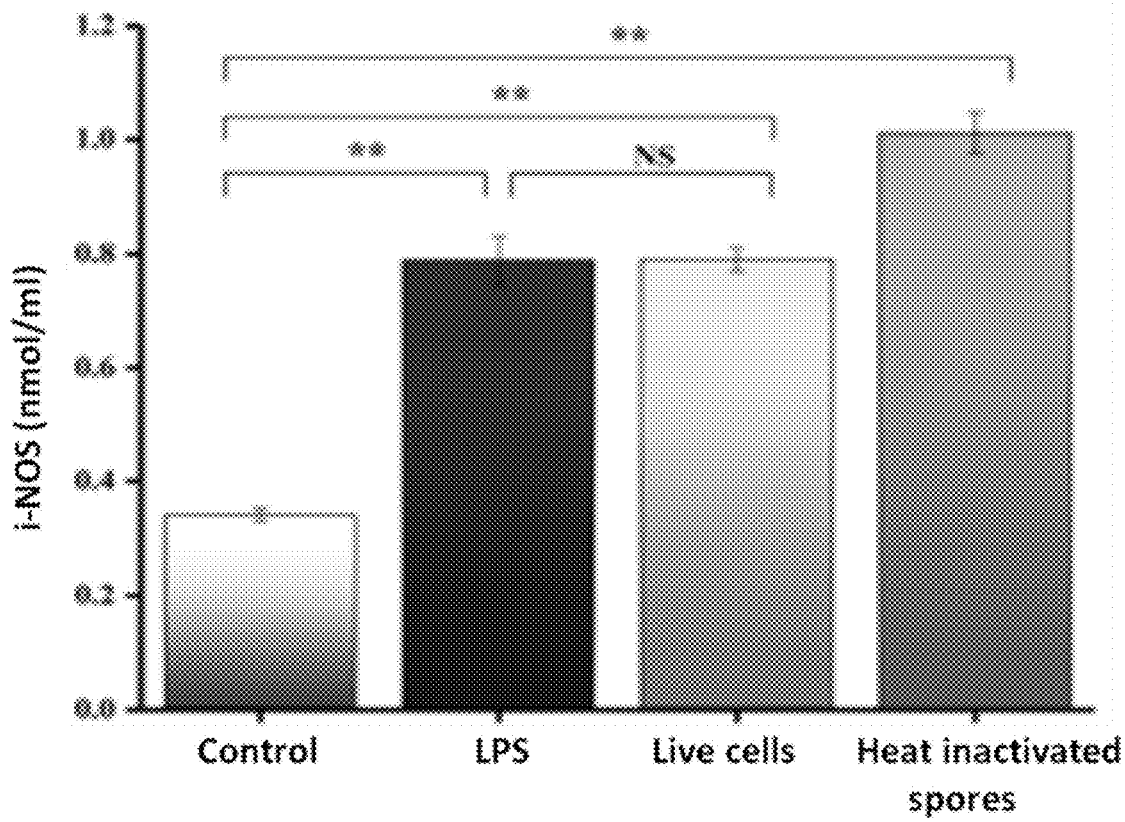
FIG. 8B is the graphical representation showing the levels of i-NOS in RAW 264.7 cells cultured with live cells, heat inactivated cells and heat inactivated spores of *Bacillus coagulans* MTCC 5856
Figure 8C:
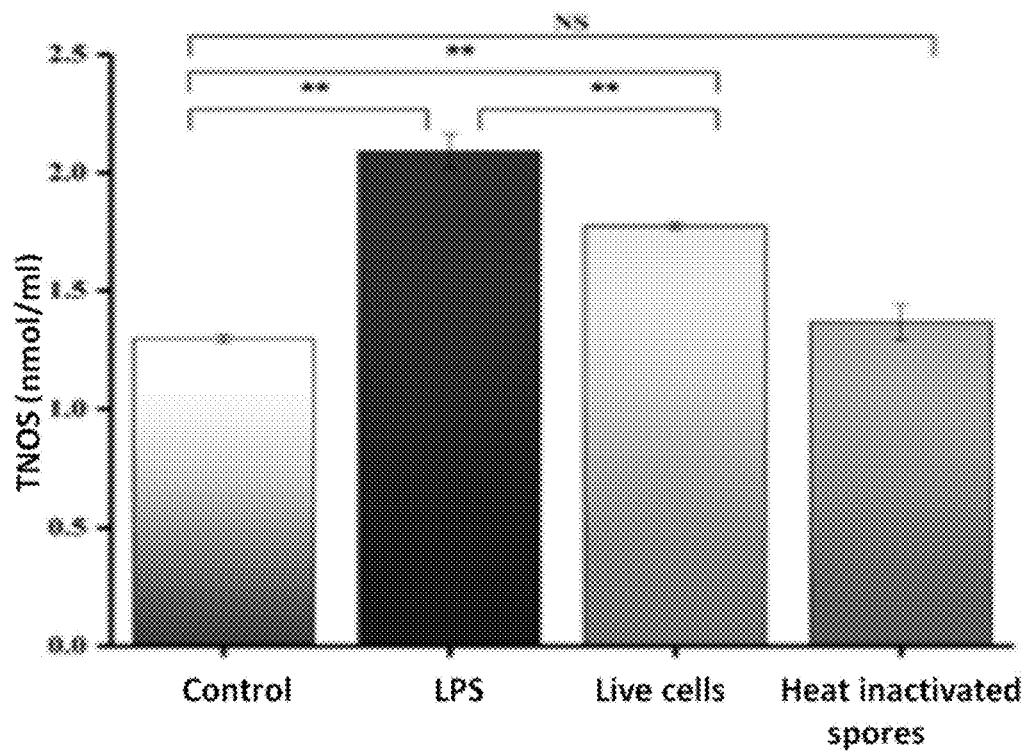
FIG. 8C is the graphical representation showing the levels of TNOS in RAW 264.7 cells cultured with live cells, heat inactivated cells and heat inactivated spores of *Bacillus coagulans* MTCC 5856
Figure 8D:
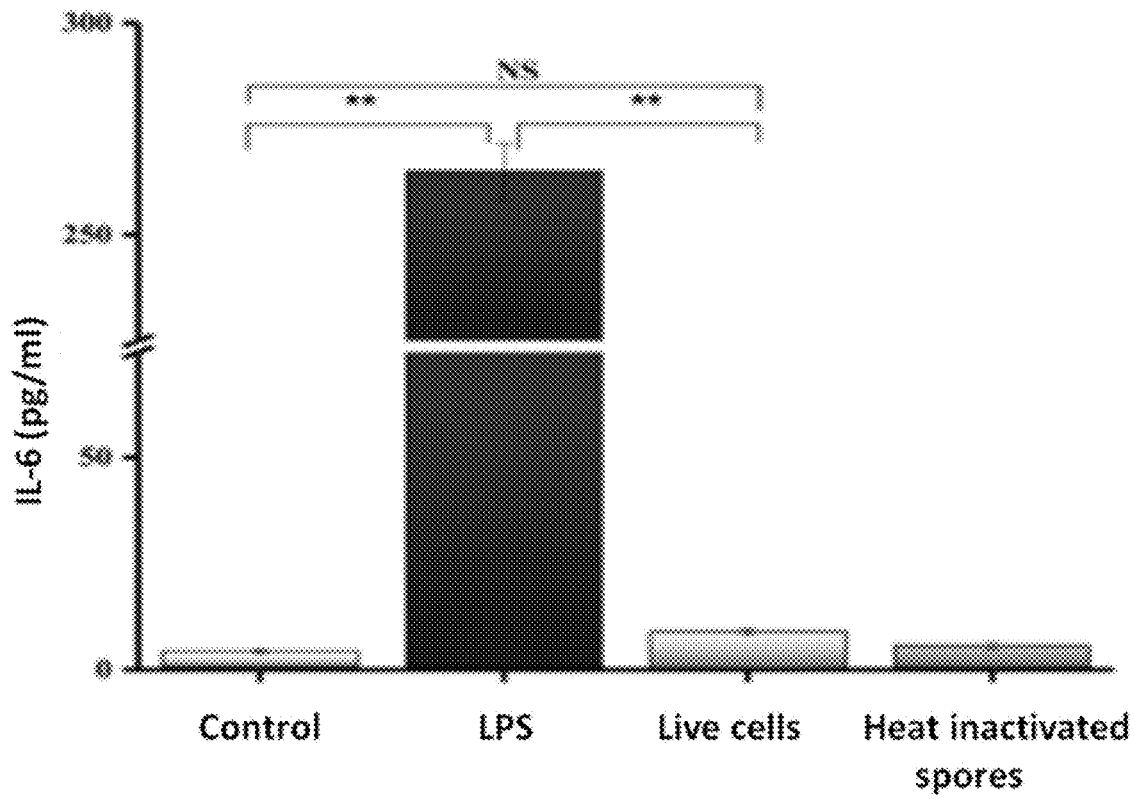
FIG. 8D is the graphical representation showing the levels of IL-6 in RAW 264.7 cells cultured with live cells, heat inactivated cells and heat inactivated spores of *Bacillus coagulans* MTCC 5856
Figure 8E:
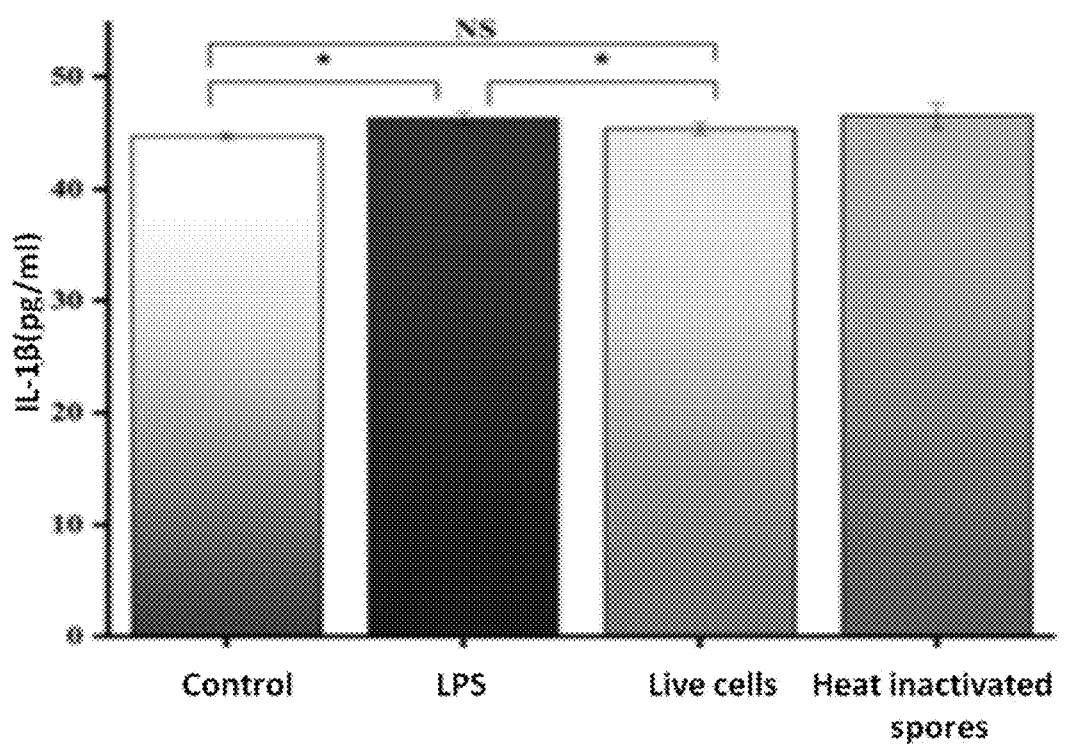
FIG. 8E is the graphical representation showing the levels of IL-1β in RAW 264.7 cells cultured with live cells, heat inactivated cells and heat inactivated spores of *Bacillus coagulans* MTCC 5856
Figure 8F:
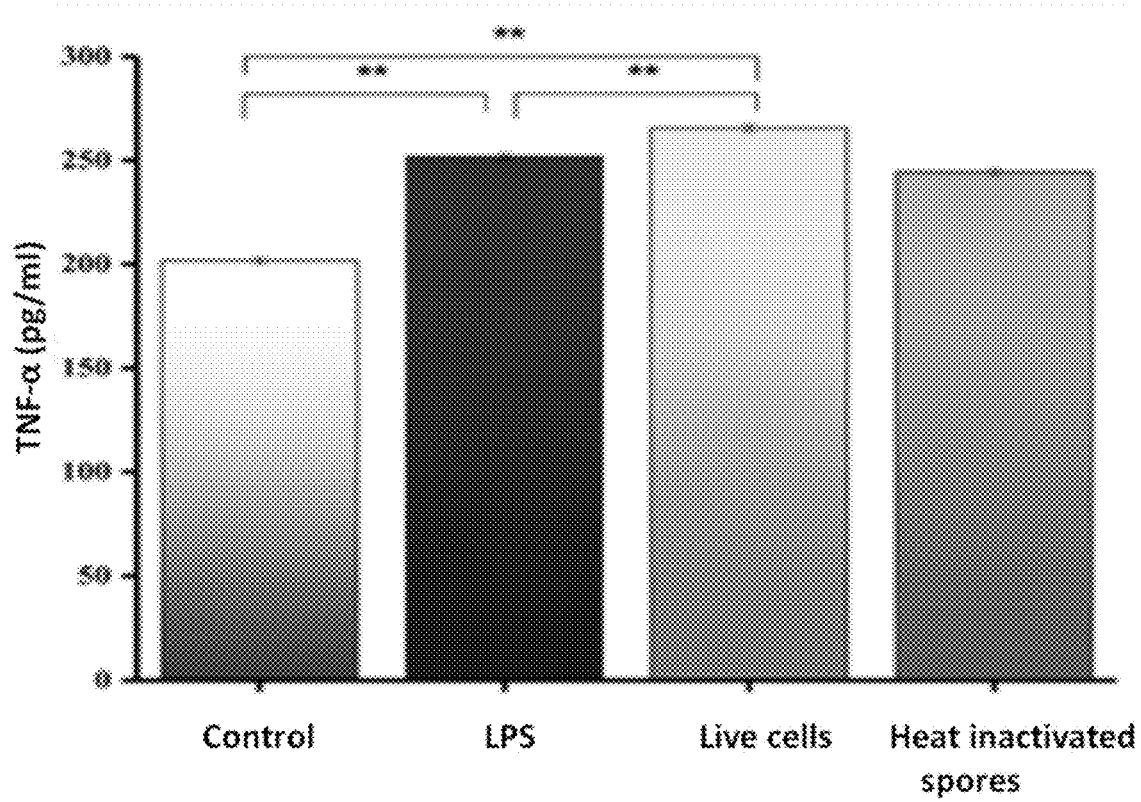
FIG. 8F is the graphical representation showing the levels of TNF-α in RAW 264.7 cells cultured with live cells, heat inactivated cells and heat inactivated spores of *Bacillus coagulans* MTCC 5856.
Figure 8G:
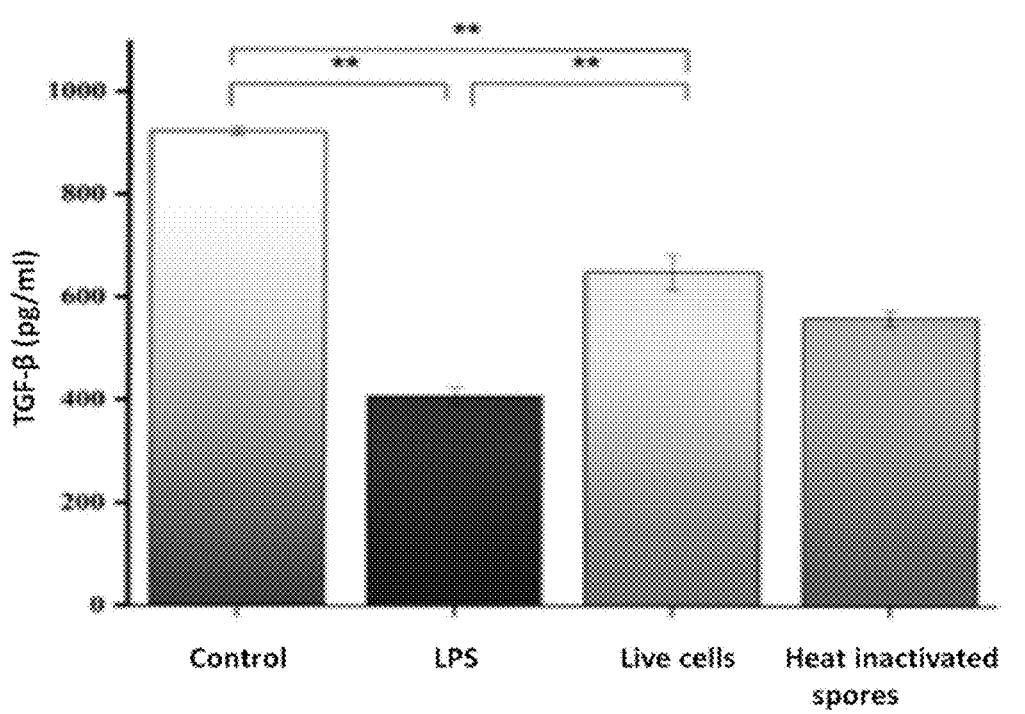
FIG. 8G is the graphical representation showing the levels of TGF-β in RAW 264.7 cells cultured with live cells, heat inactivated cells and heat inactivated spores of *Bacillus coagulans* MTCC 5856.

Cytokine profiling may indicate whether the RAW264.7 macrophages have acquired a pro-inflammatory phenotype. Hence, soluble mediators of total secreted TNOS, iNOS, NO, IL-1β, IL-6, TNF-α and TGF-β were quantified by ELISA following treatment with $1.5\times 10^8$ cfu/ml Bacillus coagulans (Live cells, heat inactivated spores) NO levels were significantly increased ($P<0.01$), compared to control samples, (FIG. 8A-8C), In particular, compared with LPS, the secretion of NO was higher with Live cells treatment. LPS was most potent in inducing cytokine IL-6 ($P<0.01$) and IL-1β ($P<0.05$) secretion (FIGS. 8D and 8E), compared to, probiotic Live cells or heat inactivated spores. Live cells were highly potent ($P<0.01$) in inducing cytokine TNF-α (FIG. 8F). Meanwhile, the amounts of secreted TGF-β were dramatically decreased ($P<0.01$) relative to control macrophages (FIG. 8G). The effects were associated with an increase in the expression of polarized-gene in macrophages co-culture with Bacillus coagulans.

Figure 9A:
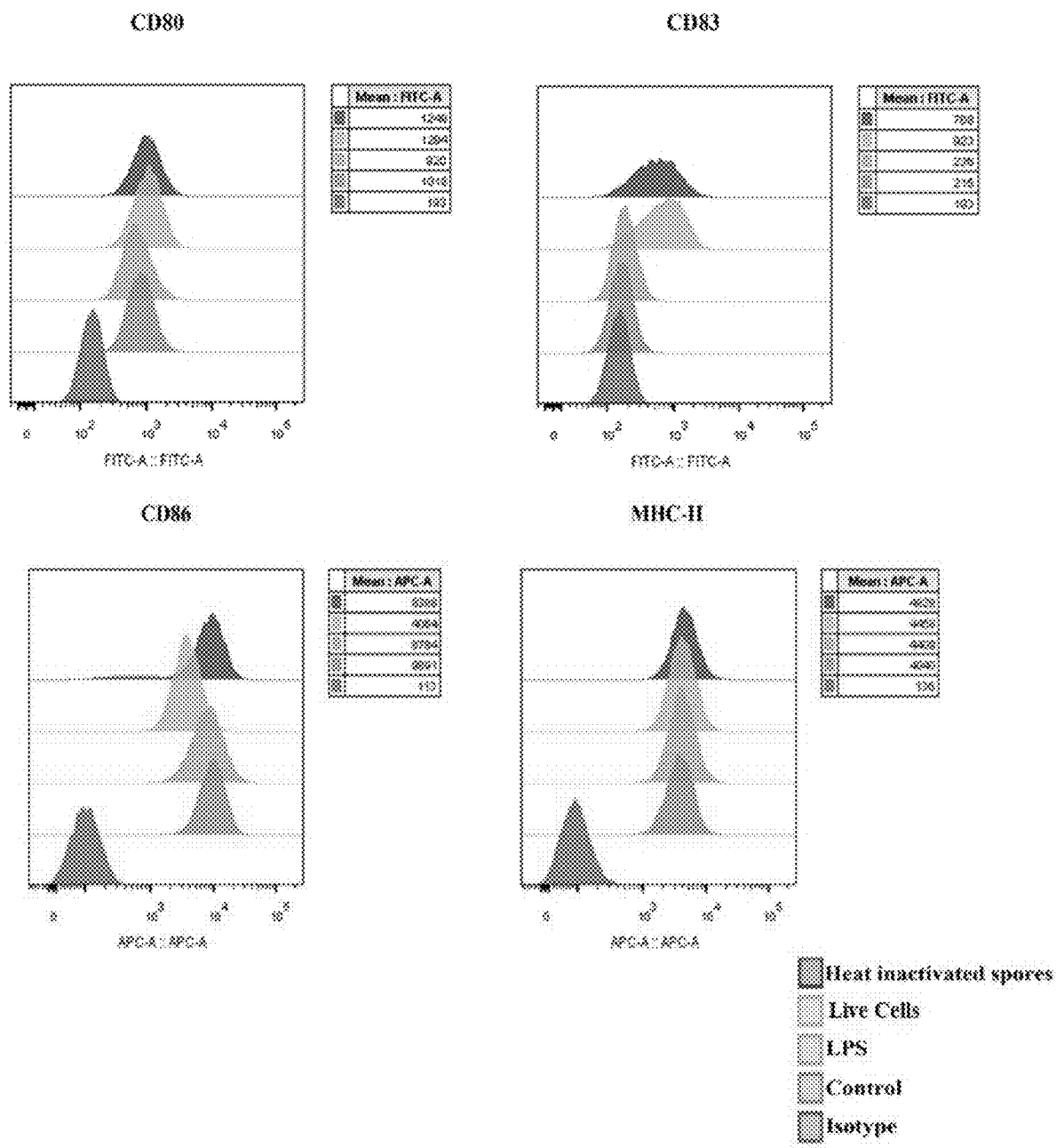
FIG. 9A is a flow cytometric graphical representation showing the effect of *Bacillus coagulans* on M1 surface receptors CD80, CD83, CD86 and MHC-II of RAW264.7 macrophages
Figure 9B:
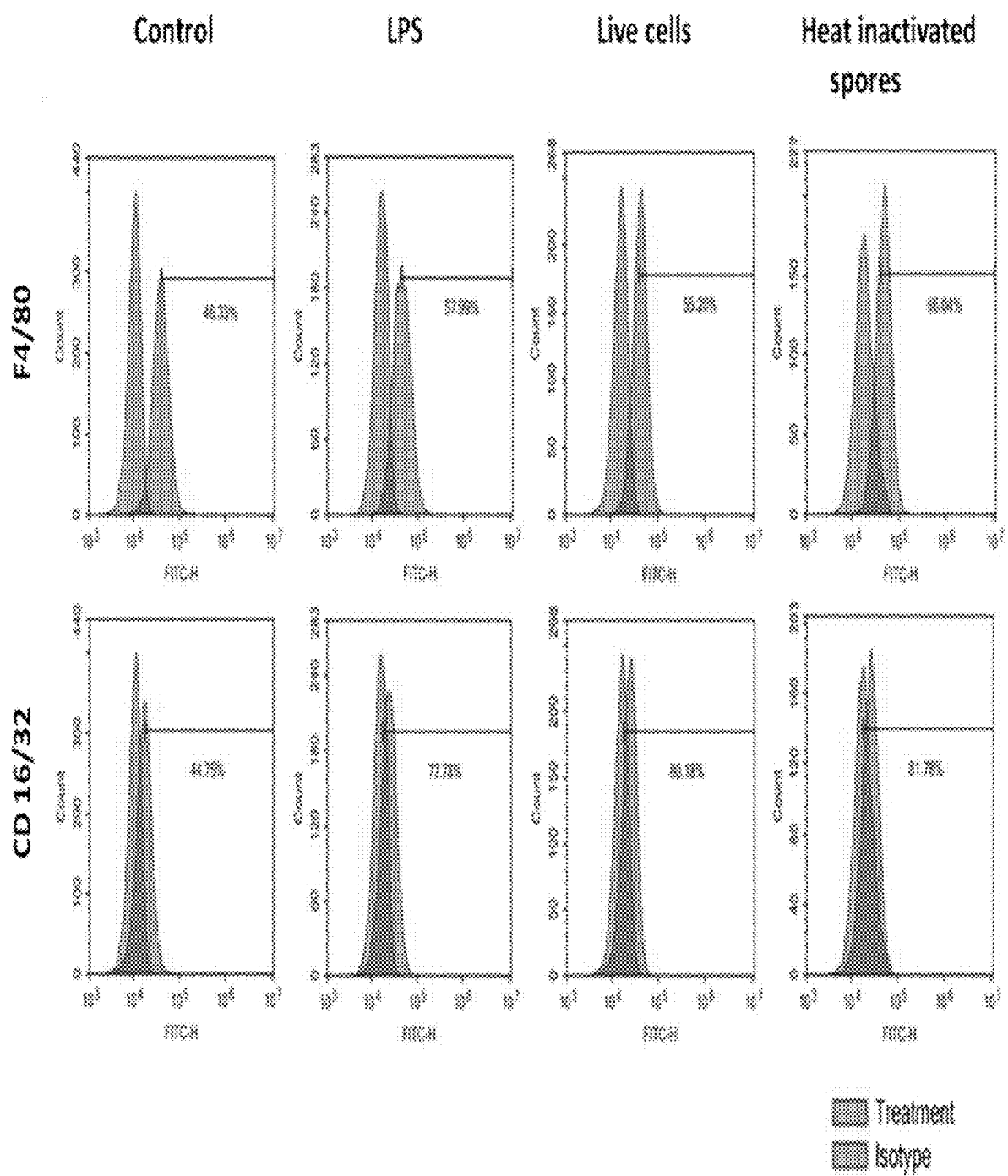
FIG. 9B is a flow cytometric graphical representation showing the effect of *Bacillus coagulans* on M1 surface receptors CD 16/32 and F 4/80 of RAW264.7 macrophages

Bacillus coagulans Promotes the Activation and Maturation of RAW264.7 Macrophages Gene analysis of M1 related and specific cytokine expressed by RAW 264.7 macrophage treated by Bacillus coagulans, indicating an activation of M1-like polarization of RAW264.7 macrophages. The expression of receptor on macrophage surfaces, including CD80, CD83, CD86, MHC-II, F4/80 and CD16/32, induced by Bacillus coagulans was confirmed by flow cytometry. The expression of the CD80 and MHC-II molecule on the surface of RAW 264.7 macrophage were lower (FIG. 9A) in cells co-cultured with $1.5\times 10^8$ cfu/ml Bacillus coagulans (Live cells, heat inactivated spores) for 6 h, relative to the PBS control group. Live bacteria not only significantly reduced CD86 expression, but also increased the CD83 cell surface marker expression, while heat inactivated spores increased CD83 and CD86 expression (FIG. 9A). The expression of Mature Mouse Macrophage Markers F4/80 and representative Receptor for M1 Polarization CD16/32 showed an higher expression in the presence of B. coagulans. Flow cytometry results demonstrated that live and heat inactivated spores could significantly polarize Raw264.7 macrophage to become M1-like macrophages, and promote cell surface antigen F4/80 and CD 16/32 expression in Raw264.7 macrophage (FIG. 9B). Above all, compared with positive LPS treatment, the activation and maturation of Raw264.7 is complicated and diversified surfaces receptor for M1 macrophage polarization.

The results indicated that both live and heat inactivated cells and spores of Bacillus coagulans induced M1 type macrophage polarisation. Since M1 polarization is important for increasing immunity against bacterial and viral infections, both live and heat inactivated spores/cells of Bacillus coagulans MTCC 5856 can be use for increasing the immunity of subjects in such need, especially in children and infants. The heat inactivated spores/cells of Bacillus coagulans MTCC 5856 can be formulated into finished products such as beverage and infant formulations and can be administered as a dietary supplement for increasing the immune function of the individual.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention. The scope of the invention is to be interpreted only in conjunction with the appended claims.

We claim:

1. A method of modulating immune function by macrophage polarization in mammals, said method comprising step of bringing into contact mammalian macrophages with an effective concentration of *Bacillus coagulans* MTCC 5856 in the form of spore or vegetative cells, to bring about the effect of immune modulation by polarizing macrophages to M1 type.

2. The method as in claim 1, wherein the spores include heat inactivated or dead spores of *Bacillus coagulans*.

3. The method as in claim 1, wherein the vegetative cells include heat inactivated or dead or lysed vegetative cells of *Bacillus coagulans*.

4. The method as in claim 1, wherein the polarisation of macrophages to M1 type is brought about by inducing the expression of pro-inflammatory genes and cells surface receptors.

5. The method as in claim 1, wherein the pro-inflammatory genes are selected from the group comprising IL-1β, IL-6, IL-12p40, IL23, TNF-α, TNOS and iNOS.

6. The method as in claim 1, wherein the cell surface receptors are selected from the group comprising CD80, CD83, CD86, MHC-II, F4/80 and CD16/32.

7. The method as in claim 1, wherein the mammal is human.

8. The method as in claim 1, wherein the composition comprising heat inactivated spores and/or vegetative cells of *Bacillus coagulans* is formulated with pharmaceutically/nutraceutically accepted excipients, adjuvants in the form of powder, infant formulation, suspension, syrup, emulsion, tablets, capsules, eatable or chewable.

* * * * *

SEQUENCE LISTING

<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Forward primer for IL 1-beta

<400> SEQUENCE: 1
gcaactgttc ctgaactcaa ct                                              22

<210> SEQ ID NO 2
<211> LENGTH: 21
<212> TYPE: DNA
<213> ORGANISM: Artificial Sequence
<220> FEATURE:
<223> OTHER INFORMATION: Reverse Primer for IL-1 Beta

<400> SEQUENCE: 2
atcttttggg gtccgtcaac t                                               21

<210> SEQ ID NO 3
<211> LENGTH: 23
<212> TYPE: DNA
<213> ORGANISM: Artificial Sequence
<220> FEATURE:
<223> OTHER INFORMATION: Forward Primer for IL-6

<400> SEQUENCE: 3
tagtccttcc taccccaatt tcc                                             23

<210> SEQ ID NO 4
<211> LENGTH: 21
<212> TYPE: DNA
<213> ORGANISM: Artificial Sequence
<220> FEATURE:
<223> OTHER INFORMATION: Reverse Primer for IL-6

<400> SEQUENCE: 4
ttggtcctta gccactcctt c                                               21

<210> SEQ ID NO 5
<211> LENGTH: 22
<212> TYPE: DNA
<213> ORGANISM: Artificial Sequence
<220> FEATURE:
<223> OTHER INFORMATION: Forward primer for IL - 12p40

<400> SEQUENCE: 5
cccattccta cttctccctc aa                                              22

<210> SEQ ID NO 6
<211> LENGTH: 22
<212> TYPE: DNA
<213> ORGANISM: Artificial Sequence
<220> FEATURE:
<223> OTHER INFORMATION: Reverse Primer for IL - 12p40

<400> SEQUENCE: 6
cctcctctgt ctccttcatc tt                                              22

<210> SEQ ID NO 7
<211> LENGTH: 23
<212> TYPE: DNA
<213> ORGANISM: Artificial Sequence

```
<220> FEATURE:
<223> OTHER INFORMATION: Forward Primer for TNF alpha

<400> SEQUENCE: 7
ccctcacact cagatcatct tct                                              23

<210> SEQ ID NO 8
<211> LENGTH: 19
<212> TYPE: DNA
<213> ORGANISM: Artificial Sequence
<220> FEATURE:
<223> OTHER INFORMATION: Reverse Primer for TNF alpha

<400> SEQUENCE: 8
gctacgacgt gggctacag                                                   19

<210> SEQ ID NO 9
<211> LENGTH: 23
<212> TYPE: DNA
<213> ORGANISM: Artificial Sequence
<220> FEATURE:
<223> OTHER INFORMATION: Forward Primer for iNOS

<400> SEQUENCE: 9
ctcacctact tcctggacat tac                                              23

<210> SEQ ID NO 10
<211> LENGTH: 21
<212> TYPE: DNA
<213> ORGANISM: Artificial Sequence
<220> FEATURE:
<223> OTHER INFORMATION: Reverse Primer for iNOS

<400> SEQUENCE: 10
caatctctgc ctatccgtct c                                                21

<210> SEQ ID NO 11
<211> LENGTH: 20
<212> TYPE: DNA
<213> ORGANISM: Artificial Sequence
<220> FEATURE:
<223> OTHER INFORMATION: Forward Primer for beta actin

<400> SEQUENCE: 11
cgttgacatc cgtaaagacc                                                  20

<210> SEQ ID NO 12
<211> LENGTH: 20
<212> TYPE: DNA
<213> ORGANISM: Artificial Sequence
<220> FEATURE:
<223> OTHER INFORMATION: Reverse Primer for beta actin

<400> SEQUENCE: 12
aacagtccgc ctagaagcac                                                  20
```